United States Patent
Ono et al.

(10) Patent No.: US 10,981,848 B2
(45) Date of Patent: Apr. 20, 2021

(54) CARBON DIOXIDE ELECTROLYTIC DEVICE AND METHOD OF ELECTROLYZING CARBON DIOXIDE

(71) Applicant: KABUSHIKI KAISHA TOSHIBA, Minato-ku (JP)

(72) Inventors: Akihiko Ono, Kita (JP); Yuki Kudo, Yokohama (JP); Ryota Kitagawa, Setagaya (JP); Masakazu Yamagiwa, Yokohama (JP); Jun Tamura, Chuo (JP); Satoshi Mikoshiba, Yamato (JP); Yoshitsune Sugano, Kawasaki (JP); Asahi Motoshige, Ota (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 246 days.

(21) Appl. No.: 16/288,145

(22) Filed: Feb. 28, 2019

(65) Prior Publication Data
US 2020/0087233 A1 Mar. 19, 2020

(30) Foreign Application Priority Data
Sep. 18, 2018 (JP) .............................. JP2018-173972

(51) Int. Cl.
*C25B 15/02* (2021.01)
*C07C 29/153* (2006.01)
(Continued)

(52) U.S. Cl.
CPC .............. *C07C 29/153* (2013.01); *C25B 1/04* (2013.01); *C25B 3/25* (2021.01); *C25B 9/73* (2021.01);
(Continued)

(58) Field of Classification Search
CPC .. C07C 29/153; G01N 27/302; G01N 33/004; Y02E 60/36; C25B 1/04; C25B 3/25;
(Continued)

(56) References Cited

U.S. PATENT DOCUMENTS

| 8,858,777 B2 * | 10/2014 | Kaczur | ..................... C25B 9/08 205/349 |
| 2018/0265440 A1 | 9/2018 | Kudo et al. | |
| 2018/0274109 A1 | 9/2018 | Kudo et al. | |

FOREIGN PATENT DOCUMENTS

WO WO 2019/181004 A1 9/2019

OTHER PUBLICATIONS

Zengcai Liu, et al., "Electrochemical generation of syngas from water and carbon dioxide at industrially important rates", Journal of $CO_2$ Utilization vol. 15, 2015, 7 pages.

(Continued)

*Primary Examiner* — Arun S Phasge
(74) *Attorney, Agent, or Firm* — Oblon, McClelland, Maier & Neustadt, L.L.P.

(57) ABSTRACT

A carbon dioxide electrolytic device includes: an electrolysis cell including a cathode, an anode, cathode and anode flow paths, and a separator; a carbon dioxide source to supply carbon dioxide to the cathode flow path; a solution source to supply an electrolytic solution containing water to the anode flow path; at least one sensor to acquire at least one data of a data indicating a discharge amount per unit time of a liquid containing water to be discharged from at least one flow path and a data indicating a concentration of at least one ion in the liquid; a refresh material source including a gas source to supply a gaseous substance to the at least one flow path; and a controller programmed to stop the supply of the carbon dioxide and the electrolytic solution, and start supply of a (Continued)

gaseous substance from the refresh material source, in accordance with the at least one data.

14 Claims, 14 Drawing Sheets

(51) Int. Cl.
  *G01N 27/30* (2006.01)
  *G01N 33/00* (2006.01)
  *C25B 1/04* (2021.01)
  *C25B 3/25* (2021.01)
  *C25B 9/73* (2021.01)
(52) U.S. Cl.
  CPC ......... *G01N 27/302* (2013.01); *G01N 33/004* (2013.01)
(58) Field of Classification Search
  CPC .......... C25B 9/73; C25B 15/02; C25B 15/08; C25B 9/19; C25B 1/00
  See application file for complete search history.

(56) References Cited

OTHER PUBLICATIONS

Sichao Ma, et al., "Efficient Electrochemical Flow System with Improved Anode for the Conversion of $CO_2$ to CO", Journal of The Electrochemical Society, 161 (10), 2014, pp. F1124-F1131.

\* cited by examiner

FIG.3
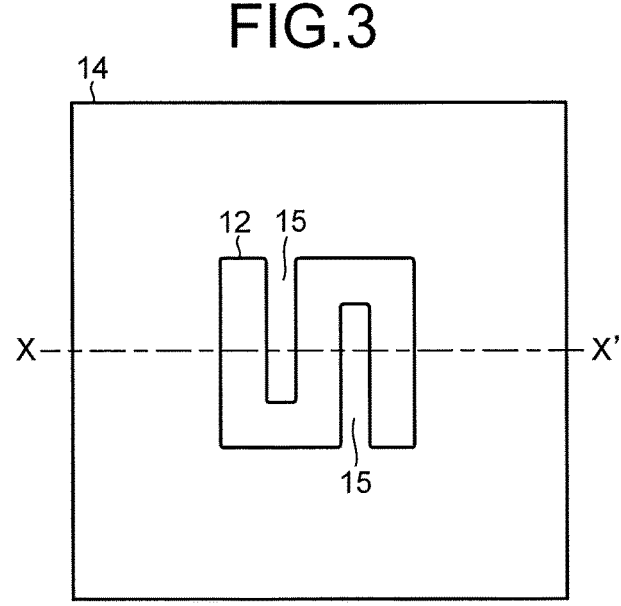
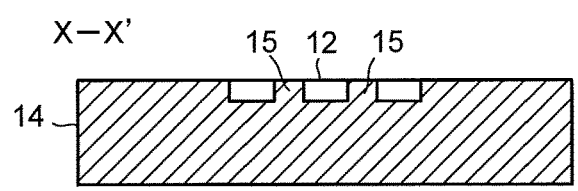
FIG.4
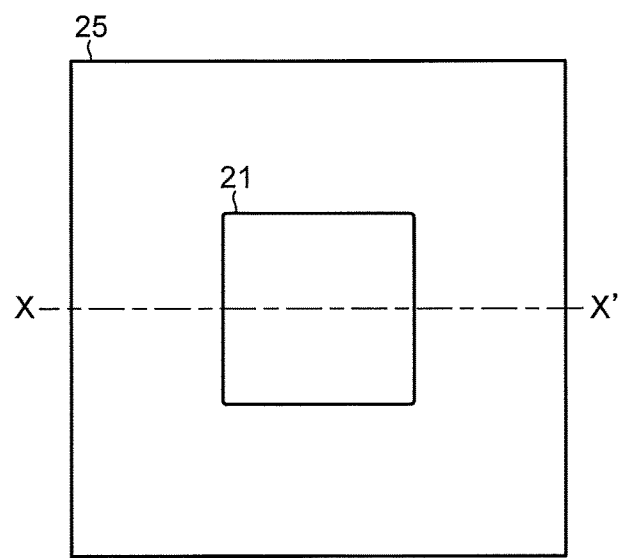
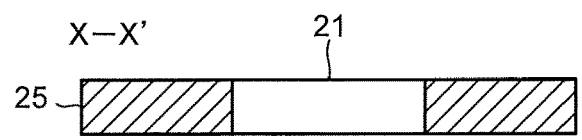

CARBON DIOXIDE ELECTROLYTIC DEVICE AND METHOD OF ELECTROLYZING CARBON DIOXIDE

CROSS REFERENCE TO RELATED APPLICATION

This application is based upon and claims the benefit of priority from Japanese Patent Application No. 2018-173972, filed on Sep. 18, 2018; the entire contents of which are incorporated herein by reference.

FIELD

Embodiments described herein generally relate to a carbon dioxide electrolytic device and a method of electrolyzing carbon dioxide.

BACKGROUND

In recent years, depletion of fossil fuel such as petroleum or coal has been concerned, and expectation for sustainably-usable renewable energy has been rising. As the renewable energy, a solar cell, wind power generation, and the like can be cited. Because a power generation amount of these depends on weather and a natural situation, there is a problem that it is difficult to realize stable supply of electric power. For this reason, there has been made an attempt to store the electric power generated by the renewable energy in a storage battery, to thereby stabilize the electric power. However, when the electric power is stored, there are problems that a cost is required for the storage battery, and a loss occurs at a time of the storage.

With respect to such points, attention is focused on a technology in which water electrolysis is performed by using the electric power generated by the renewable energy to produce hydrogen ($H_2$) from water, or carbon dioxide ($CO_2$) is electrochemically reduced to be converted into a chemical substance (chemical energy) such as a carbon compound such as carbon monoxide (CO), formic acid (HCOOH), methanol ($CH_3OH$), methane ($CH_4$), acetic acid ($CH_3COOH$), ethanol ($C_2H_5OH$), ethane ($C_2H_6$), or ethylene ($C_2H_4$). When these chemical substances are stored in a cylinder or a tank, there are advantageous points that a storage cost of energy can be reduced, and a storage loss is also small, when compared to a case where the electric power (electric energy) is stored in the storage battery.

As a carbon dioxide electrolytic device, for example, a structure in which an Ag nanoparticle catalyst is used as a cathode, a cathode solution and $CO_2$ gas are brought into contact with the cathode, and an anode solution is brought into contact with an anode is being studied. As a concrete configuration of the electrolytic device, for example, there can be cited a configuration which includes a cathode solution flow path disposed along one surface of the cathode, a $CO_2$ gas flow path disposed along the other surface of the cathode, an anode solution flow path disposed along one surface of an anode, and a separator disposed between the cathode solution flow path and the anode solution flow path. When a reaction of producing, for example, CO from $CO_2$ is performed for a long period of time by using the electrolytic device having such a configuration and, for example, by making a constant current flow through the cathode and the anode, there is a problem that a deterioration over time of a cell performance such that a production amount of CO is reduced or a cell voltage is increased occurs. For this reason, there has been demanded a carbon dioxide electrolytic device capable of suppressing the deterioration over time of the cell performance.

BRIEF DESCRIPTION OF THE DRAWINGS

FIG. 3 is a view illustrating one example of an anode solution flow path in the electrolysis cell illustrated in FIG. 2.

FIG. 4 is a view illustrating one example of a cathode solution flow path in the electrolysis cell illustrated in FIG. 2.

DETAILED DESCRIPTION

A carbon dioxide electrolytic device of an embodiment comprises: an electrolysis cell including a cathode to reduce a first substance containing carbon dioxide and thus produce a first product containing a carbon compound, an anode to oxidize a second substance containing water or hydroxide ions and thus produce a second product containing oxygen, a cathode flow path facing the cathode, an anode flow path facing the anode, and a separator separating the anode and the cathode; a carbon dioxide source to supply the carbon dioxide to the cathode flow path; a solution source to supply an electrolytic solution containing water to the anode flow path; at least one sensor to acquire at least one data selected from the group consisting of a data indicating a discharge amount per unit time of a liquid containing water to be discharged from at least one flow path selected from the group consisting of the anode and cathode flow paths and a data indicating a concentration of at least one ion selected from the group consisting of ions in the liquid; a power controller to apply a voltage between the anode and the cathode; a refresh material source including a gas source to supply a gaseous substance to the at least one flow path; and a controller programmed to stop the supply of the carbon dioxide and the electrolytic solution, and start the supply of the gaseous substance from the refresh material source to the at least one flow path, in accordance with the at least one data.

Hereinafter, a carbon dioxide electrolytic device of an embodiment will be described with reference to the drawings. In each embodiment presented below, substantially the same components are denoted by the same reference signs, and a description thereof is sometimes partially omitted. The drawings are schematic, and a relationship between a thickness and a planar size, thickness proportions of the respective portions, and the like are sometimes different from actual ones.

First Embodiment

Figure 1:
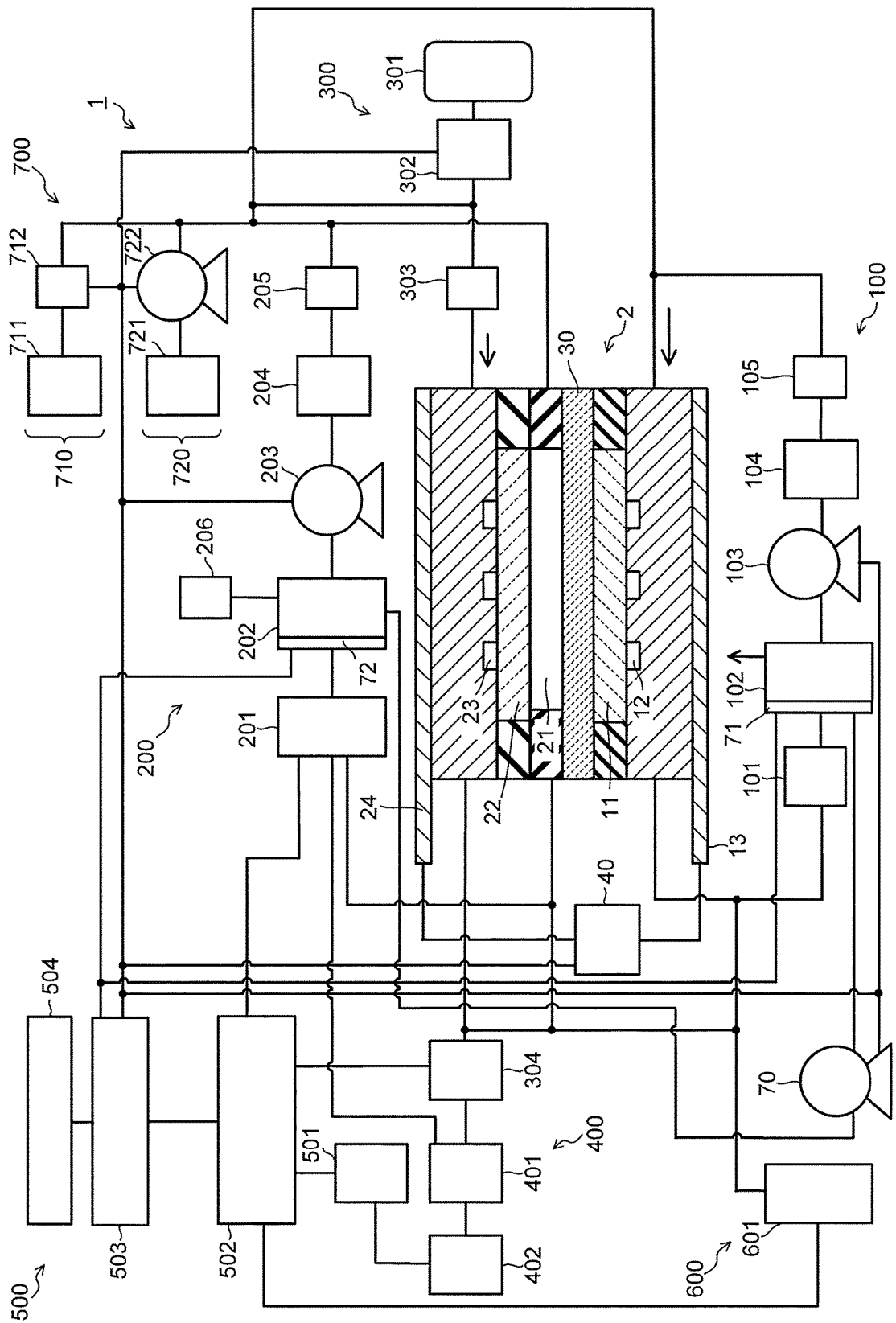
FIG. 1 is a view illustrating a carbon dioxide electrolytic device of a first embodiment.
Figure 2:
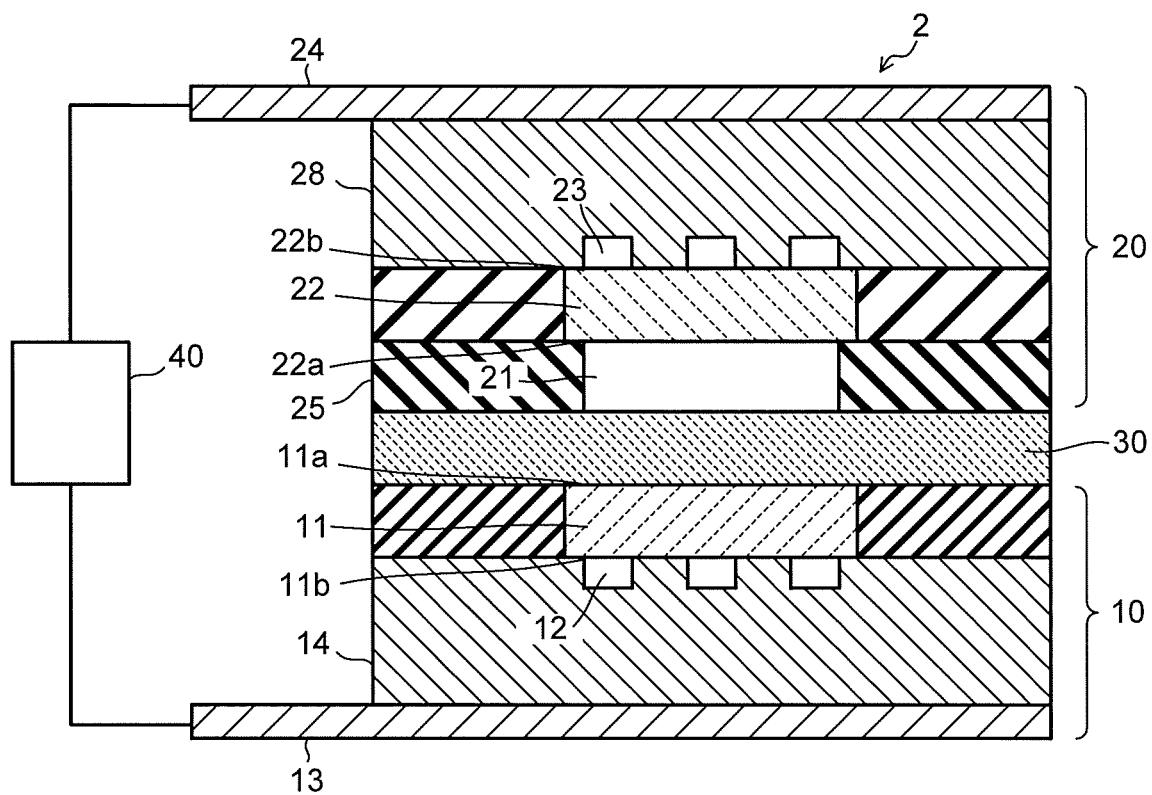
FIG. 2 is a sectional view illustrating an electrolysis cell of the carbon dioxide electrolytic device illustrated in FIG. 1.

FIG. 1 is a view illustrating a configuration of a carbon dioxide electrolytic device according to a first embodiment, and FIG. 2 is a sectional view illustrating a configuration of an electrolysis cell in the electrolytic device illustrated in FIG. 1. A carbon dioxide electrolytic device 1 illustrated in FIG. 1 includes an electrolysis cell 2, an anode solution supply system 100 which supplies an anode solution to the electrolysis cell 2, a cathode solution supply system 200 which supplies a cathode solution to the electrolysis cell 2, a gas supply system 300 which supplies carbon dioxide ($CO_2$) gas to the electrolysis cell 2, a product collection system 400 which collects a product produced by a reduction reaction in the electrolysis cell 2, a control system 500 which detects a type and a production amount of the collected product, and performs control of the product and control of a refresh operation, a waste solution collection system 600 which collects a waste solution of the cathode solution and the anode solution, and a refresh material source 700 which recovers an anode, a cathode, or the like of the electrolysis cell 2.

As illustrated in FIG. 2, the electrolysis cell 2 includes an anode part 10, a cathode part 20, and a separator 30. The anode part 10 includes an anode 11, an anode flow path 12 (anode solution flow path), and an anode current collector 13. The cathode part 20 includes a cathode flow path 21 (cathode solution flow path), a cathode 22, a cathode flow path 23 ($CO_2$ gas flow path), and a cathode current collector 24. The cathode solution flow path may not be provided. The separator 30 is disposed to separate the anode part 10 and the cathode part 20. The electrolysis cell 2 is sandwiched by a pair of support plates, which are not illustrated, and further tightened by bolts or the like. In FIG. 1 and FIG. 2, there is provided a power controller 40 which makes a current flow through the anode 11 and the cathode 22. The power controller 40 is connected to the anode 11 and the cathode 22 via a current introduction member. The power controller 40 is not limited to a normal system power supply, battery, or the like, and may be one having a power source which supplies electric power generated by renewable energy such as a solar cell or wind power generation. Note that the power controller 40 may also have the aforementioned power source and a power controller or the like that adjusts an output of the aforementioned power source to control a voltage between the anode 11 and the cathode 22.

The anode 11 is an electrode (oxidation electrode) which causes an oxidation reaction of water ($H_2O$) in an anode solution as an electrolytic solution to produce oxygen ($O_2$) or hydrogen ions ($H^+$), or causes an oxidation reaction of hydroxide ions ($OH^-$) produced in the cathode part 20 to produce oxygen ($O_2$) or water ($H_2O$). The anode 11 has a first surface 11a which is brought into contact with the separator 30, and a second surface 11b which faces the anode flow path 12. The first surface 11a of the anode 11 is brought into close contact with the separator 30. The anode flow path 12 supplies the anode solution to the anode 11, and is formed of a pit (groove portion/concave portion) provided in a first flow path plate 14. The anode solution flows through inside the anode flow path 12 so as to be brought into contact with the anode 11. The anode current collector 13 is electrically brought into contact with a surface on a side opposite to the anode 11 of the first flow path plate 14 which forms the anode flow path 12.

As described above, in the electrolysis cell 2 of the embodiment, the anode 11 and the separator 30 are brought into close contact with each other. In the anode 11, oxygen ($O_2$) is produced, and at this time, in a cell structure in which a separator is sandwiched by a cathode solution flow path and an anode solution flow path, air bubbles of oxygen ($O_2$) gas generated in the anode 11 stay in the anode solution flow path, and a cell resistance between the anode and the separator (ion exchange membrane or the like) increases, this sometimes increases a voltage variation of the anode. With respect to a point as above, the anode flow path 12 is not disposed between the anode 11 and the separator 30, and by making the anode 11 and the separator 30 to be brought into close contact with each other, oxygen gas generated in the anode 11 is discharged to the anode flow path 12 together with the anode solution. This makes it possible to prevent the oxygen gas from staying between the anode 11 and the separator 30, and it becomes possible to suppress a variation in a cell voltage due to the voltage variation of the anode.

To the first flow path plate 14, there are provided a solution inlet port and a solution outlet port whose illustrations are omitted, and the anode solution is introduced and discharged by the anode solution supply system 100 via these solution inlet port and solution outlet port. It is preferable to use a material having low chemical reactivity and high conductivity for the first flow path plate 14. As such a material, there can be cited a metal material such as Ti or SUS, carbon, or the like. It is preferable that the anode flow path 12 is provided with a plurality of lands (convex portions) 15, as illustrated in FIG. 3. The lands 15 are provided for mechanical retention and electrical continuity. The lands 15 are preferably provided in an alternate manner for uniformizing the flow of the anode solution. Since the lands 15 as above are provided, the anode flow path 12 meanders. In addition, also for the purpose of realizing good discharge of the anode solution containing oxygen ($O_2$) gas mixed therein, it is preferable that the lands 15 are provided in an alternate manner to the anode flow path 12 to make the anode flow path 12 meander.

It is preferable that the anode 11 is mainly constituted of a catalyst material (anode catalyst material) capable of oxidizing water ($H_2O$) to produce oxygen or hydrogen ions or oxidizing hydroxide ions ($OH^-$) to produce water or oxygen, and capable of reducing an overvoltage in such a reaction. As such a catalyst material, there can be cited a metal such as platinum (Pt), palladium (Pd), or nickel (Ni), an alloy or an intermetallic compound containing the above metals, a binary metal oxide such as a manganese oxide (Mn—O), an iridium oxide (Ir—O), a nickel oxide (Ni—O), a cobalt oxide (Co—O), an iron oxide (Fe—O), a tin oxide (Sn—O), an indium oxide (In—O), a ruthenium oxide (Ru—O), a lithium oxide (Li—O), or a lanthanum oxide (La—O), a ternary metal oxide such as Ni—Co—O, Ni—Fe—O, La—Co—O, Ni—La—O, or Sr—Fe—O, a quaternary metal oxide such as Pb—Ru—Ir—O or La—Sr—Co—O, or a metal complex such as a Ru complex or an Fe complex.

The anode 11 includes a base material having a structure capable of making the anode solution or ions move between the separator 30 and the anode flow path 12, for example, a porous structure such as a mesh material, a punching material, a porous body, or a metal fiber sintered body. The base material may be constituted of a metal such as titanium (Ti), nickel (Ni), or iron (Fe), or a metal material such as an alloy (for example, SUS) containing at least one of these metals, or may be constituted of the above-described anode catalyst material. When an oxide is used as the anode catalyst material, it is preferable to form a catalyst layer in a manner that the anode catalyst material is adhered to or stacked on a surface of the base material made of the above-described metal material. The anode catalyst material preferably has nanoparticles, a nanostructure, a nanowire, or the like for the purpose of increasing the oxidation reaction. The nanostructure is a structure in which nanoscale irregularities are formed on a surface of the catalyst material.

The cathode 22 is an electrode (reduction electrode) which causes a reduction reaction of carbon dioxide ($CO_2$) or a reduction reaction of a carbon compound produced thereby to produce a carbon compound such as carbon monoxide (CO), methane ($CH_4$), ethane ($C_2H_6$), ethylene ($C_2H_4$), methanol ($CH_3OH$), ethanol ($C_2H_5OH$), or ethylene glycol ($C_2H_6O_2$). In the cathode 22, there is a case where a side reaction in which hydrogen ($H_2$) is produced by a reduction reaction of water ($H_2O$) is caused simultaneously with the reduction reaction of carbon dioxide ($CO_2$). The cathode 22 has a first surface 22a facing the cathode flow path 21, and a second surface 22b facing the cathode flow path 23. The cathode flow path 21 is disposed between the cathode 22 and the separator 30 so that the cathode solution as an electrolytic solution is brought into contact with the cathode 22 and the separator 30.

The cathode flow path 21 is formed of an opening portion provided in a flow path plate 25. To the flow path plate 25, there are provided a solution inlet port and a solution outlet port whose illustrations are omitted, and the cathode solution is introduced and discharged by the cathode solution supply system 200 via these solution inlet port and solution outlet port. The cathode solution flows through inside the cathode flow path 21 so as to be brought into contact with the cathode 22 and the separator 30. It is preferable to use a material having low chemical reactivity and having no conductivity for the flow path plate 25 forming the cathode flow path 21. As such a material, there can be cited an insulating resin material such as an acrylic resin, polyetheretherketone (PEEK), or a fluorocarbon resin.

Figure 5:
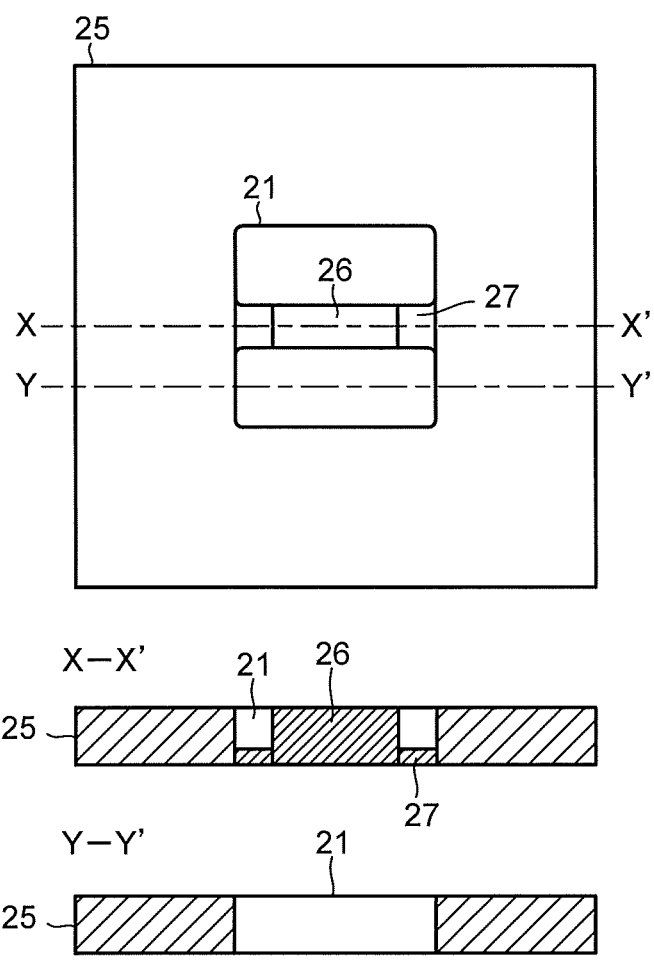
FIG. 5 is a view illustrating another example of the cathode solution flow path in the electrolysis cell illustrated in FIG. 2.

In the cathode 22, the reduction reaction of $CO_2$ occurs mainly in a portion which is brought into contact with the cathode solution. For this reason, it is preferable to apply an opening portion with a wide opening area to the cathode flow path 21, as illustrated in FIG. 4. However, in order to increase the mechanical retention and the electrical connectivity, it is also possible to provide a land (convex portion) 26 to the cathode flow path 21, as illustrated in FIG. 5. The land 26 of the cathode flow path 21 is provided at a center portion of the cathode flow path 21, and is retained to the flow path plate 25 by a bridge portion 27 which is thinner than the land 26, in order not to prevent the flow of the cathode solution in the cathode flow path 21. When the land 26 is provided to the cathode flow path 21, the number of lands 26 is preferably small in order to reduce a cell resistance.

The cathode flow path 23 is formed of a pit (groove portion/concave portion) provided in a flow path plate 28. It is preferable to use a material having low chemical reactivity and high conductivity for the flow path plate 28 forming the $CO_2$ gas flow path. As such a material, there can be cited a metal material such as Ti or SUS, carbon, or the like. Note that in each of the first flow path plate 14, the flow path plate 25, and the flow path plate 28, an inlet port and an outlet port for a solution or gas, screw holes for tightening, and the like, whose illustrations are omitted, are provided. Further, in front of and behind each of the flow path plates 14, 25, and 28, packing whose illustration is omitted is sandwiched according to need.

Figure 6:
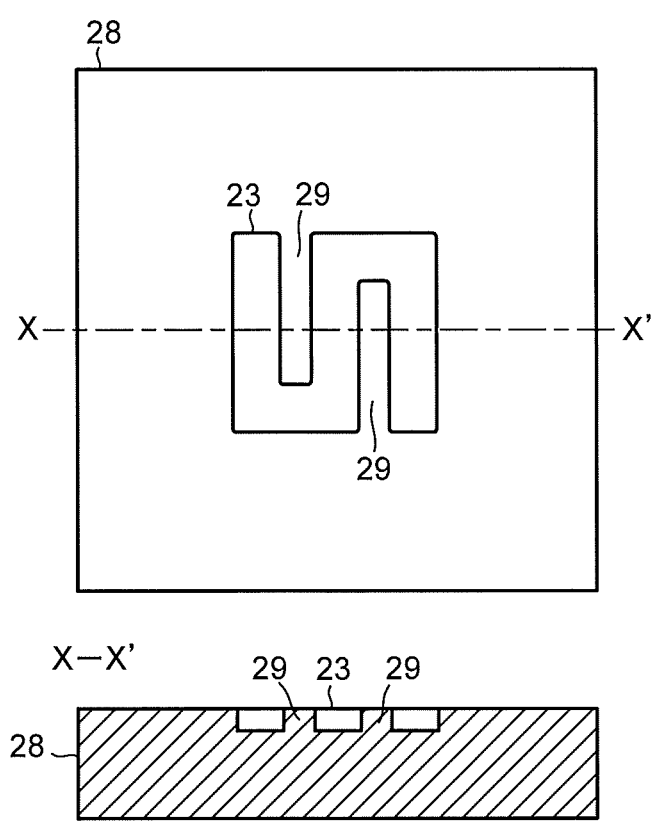
FIG. 6 is a view illustrating one example of a $CO_2$ gas flow path in the electrolysis cell illustrated in FIG. 2.

To the flow path plate 28, a gas inlet port and a gas outlet port whose illustrations are omitted are provided, and $CO_2$ gas or gas containing $CO_2$ (sometimes collectively referred to simply as $CO_2$ gas) is introduced and discharged by the gas supply system 300 via these gas inlet port and gas outlet port. The $CO_2$ gas flows through inside the cathode flow path 23 so as to be brought into contact with the cathode 22. It is preferable that the cathode flow path 23 is provided with a plurality of lands (convex portions) 29, as illustrated in FIG. 6. The lands 29 are provided for mechanical retention and electrical continuity. The lands 29 are preferably provided in an alternate manner, which realizes a state where the cathode flow path 23 meanders similarly to the anode flow path 12. The cathode current collector 24 is electrically brought into contact with a surface on a side opposite to the cathode 22 of the flow path plate 28.

In the electrolysis cell 2 of the embodiment, by providing the lands 15 and 29 to the anode flow path 12 and the cathode flow path 23, it is possible to increase a contact area between the anode 11 and the first flow path plate 14 forming the anode flow path 12, and a contact area between the cathode 22 and the flow path plate 28 forming the cathode flow path 23. Further, by providing the land 26 to the cathode flow path 21, it is possible to increase a contact area between the cathode 22 and the flow path plate 25 forming the cathode flow path 21. These realize good electrical continuity between the anode current collector 13 and the cathode current collector 24 while enhancing mechanical retentivity of the electrolysis cell 2, and it becomes possible to improve reduction reaction efficiency of $CO_2$, and the like. The cathode flow path 21 causes increase in the cell resistance, and thus it may not be provided.

Figure 7:
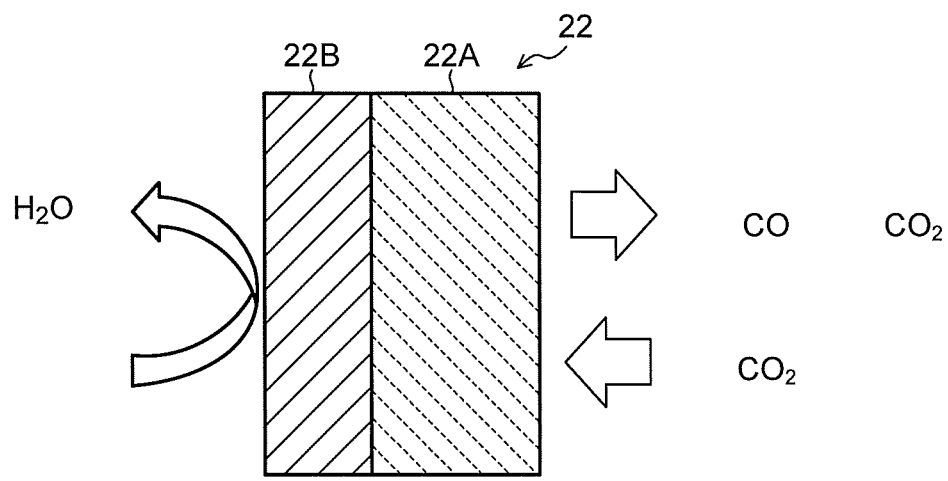
FIG. 7 is a view illustrating one example of a cathode in the electrolysis cell illustrated in FIG. 2.
Figure 8:
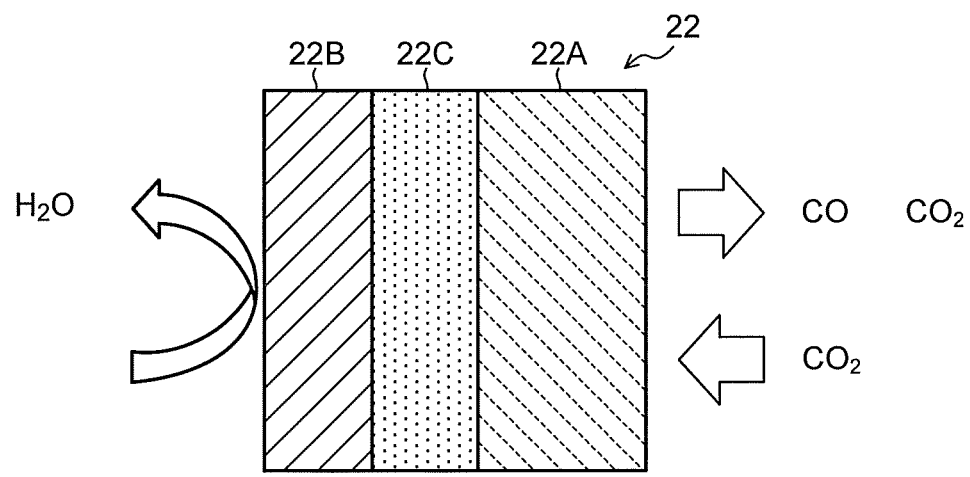
FIG. 8 is a view illustrating another example of the cathode in the electrolysis cell illustrated in FIG. 2.
Figure 9:
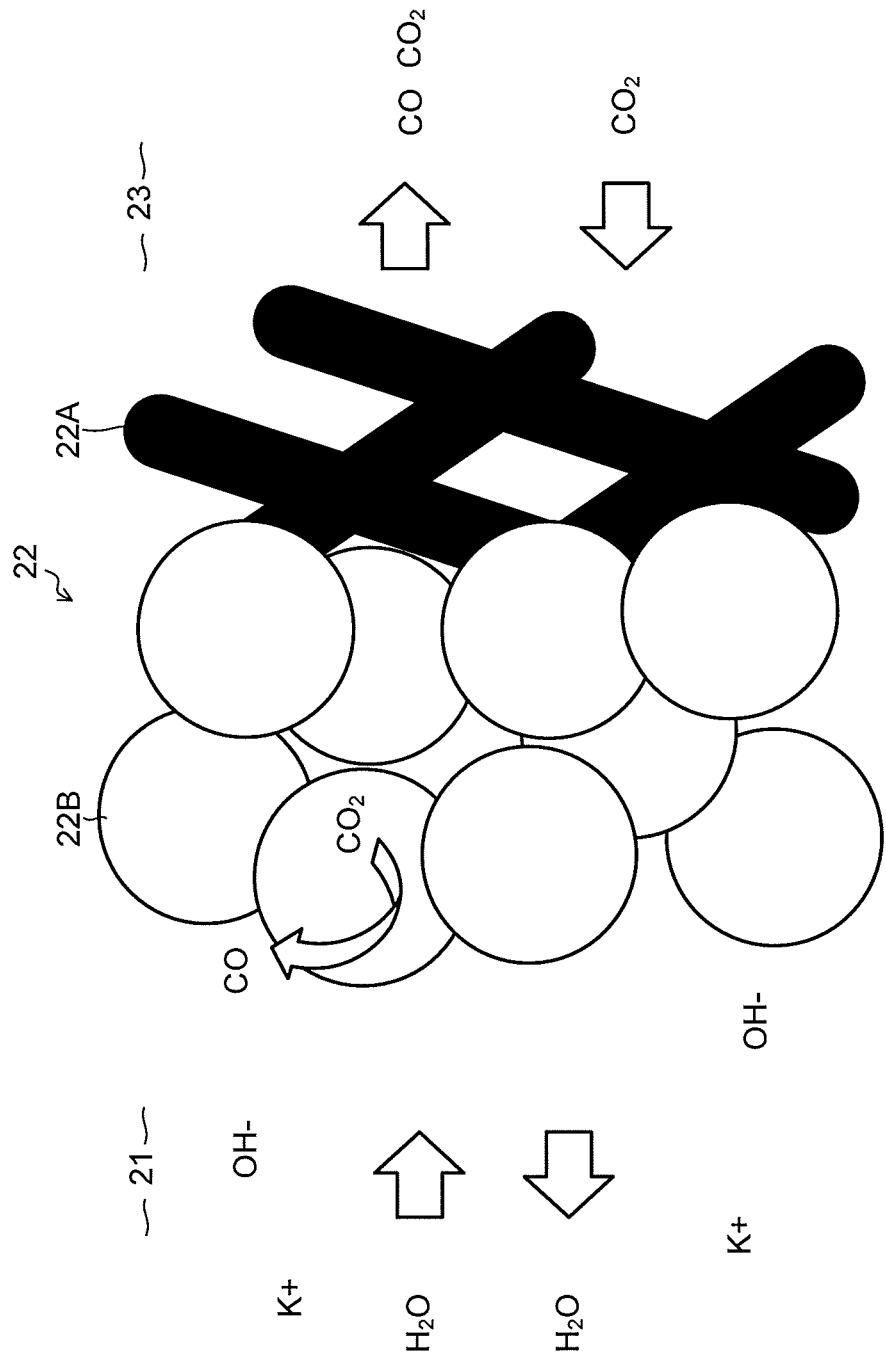
FIG. 9 is a view schematically illustrating a reaction in the cathode in the electrolysis cell illustrated in FIG. 2.

As illustrated in FIG. 7, the cathode 22 has a gas diffusion layer 22A and a cathode catalyst layer 22B provided on the gas diffusion layer 22A. As illustrated in FIG. 8, it is also possible that a porous layer 22C denser than the gas diffusion layer 22A is disposed between the gas diffusion layer 22A and the cathode catalyst layer 22B. As illustrated in FIG. 9, the gas diffusion layer 22A is disposed on the cathode flow path 23 side, and the cathode catalyst layer 22B is disposed on the cathode flow path 21 side. The cathode catalyst layer 22B may enter the gas diffusion layer 22A. The cathode catalyst layer 22B preferably has catalyst nanoparticles, a catalyst nanostructure, or the like. The gas diffusion layer 22A is constituted of, for example, carbon paper, carbon cloth, or the like, and water repellent treatment is performed thereon. The porous layer 22C is constituted of a porous body whose pore size is smaller than that of the carbon paper or the carbon cloth.

As illustrated in a schematic view in FIG. 9, in the cathode catalyst layer 22B, the cathode solution or ions are supplied and discharged from the cathode flow path 21. In the gas diffusion layer 22A, the $CO_2$ gas is supplied from the cathode flow path 23, and a product obtained by the reduction reaction of the $CO_2$ gas is discharged. By previously performing moderate water repellent treatment on the gas diffusion layer 22A, the $CO_2$ gas reaches the cathode catalyst layer 22B mainly through gas diffusion. The reduction reaction of $CO_2$ or the reduction reaction of a carbon compound produced thereby occurs in the vicinity of a boundary between the gas diffusion layer 22A and the cathode catalyst layer 22B or in the vicinity of the cathode catalyst layer 22B which enters the gas diffusion layer 22A, a gaseous product is discharged mainly from the cathode flow path 23, and a liquid product is discharged mainly from the cathode flow path 21. When there is no cathode flow path 21, the cathode catalyst layer 22B and the separator 30 are brought into contact with each other.

The cathode catalyst layer 22B is preferably constituted of a catalyst material (cathode catalyst material) capable of reducing carbon dioxide to produce a carbon compound, capable of reducing the carbon compound produced thereby to produce a carbon compound according to need, and capable of reducing an overvoltage in the above reaction. As such a material, there can be cited a metal such as gold (Au), silver (Ag), copper (Cu), platinum (Pt), palladium (Pd), nickel (Ni), cobalt (Co), iron (Fe), manganese (Mn), titanium (Ti), cadmium (Cd), zinc (Zn), indium (In), gallium (Ga), lead (Pb), or tin (Sn), a metal material such as an alloy or an intermetallic compound containing at least one of the above metals, a carbon material such as carbon (C), graphene, CNT (carbon nanotube), fullerene, or ketjen black, or a metal complex such as a Ru complex or a Re complex. The cathode catalyst layer 22B can employ various shapes such as a plate shape, a mesh shape, a wire shape, a particle shape, a porous shape, a thin film shape, and an island shape.

The cathode catalyst material constituting the cathode catalyst layer 22B preferably has nanoparticles of the above-described metal material, a nanostructure of the metal material, a nanowire of the metal material, or a composite body in which the nanoparticles of the above-described metal material are supported by a carbon material such as carbon particles, a carbon nanotube, or graphene. By applying catalyst nanoparticles, a catalyst nanostructure, a catalyst nanowire, a catalyst nano-support structure, or the like as the cathode catalyst material, it is possible to increase reaction efficiency of the reduction reaction of carbon dioxide in the cathode 22.

The separator 30 is constituted of an ion exchange membrane or the like capable of making ions move between the anode 11 and the cathode 22, and capable of separating the anode part 10 and the cathode part 20. As the ion exchange membrane, it is possible to use, for example, a cation exchange membrane such as Nafion or Flemion, or an anion exchange membrane such as Neosepta or Selemion. As will be described later, when an alkaline solution is used as the anode solution and the cathode solution, and it is assumed that hydroxide ions ($OH^-$) move mainly, the separator 30 is preferably constituted of the anion exchange membrane. However, other than the ion exchange membrane, it is also possible to apply a glass filter, a porous polymeric membrane, a porous insulating material, or the like to the separator 30, as long as they are a material capable of making ions move between the anode 11 and the cathode 22.

Each of the anode solution and the cathode solution as the electrolytic solution is preferably a solution containing at least water ($H_2O$). Because carbon dioxide ($CO_2$) is supplied from the cathode flow path 23, the cathode solution may contain or need not contain carbon dioxide ($CO_2$). To the anode solution and the cathode solution, the same solution may be applied or different solutions may be applied. As a solution containing $H_2O$ used as the anode solution and the cathode solution, an aqueous solution containing an arbitrary electrolyte can be cited. As the aqueous solution containing the electrolyte, there can be cited, for example, an aqueous solution containing at least one selected from a hydroxide ion ($OH^-$), a hydrogen ion ($H^1$), a potassium ion ($K^1$), a sodium ion ($Na^1$), a lithium ion ($Li^+$), a chloride ion ($Cl^-$), a bromide ion ($Br^-$), an iodide ion ($I^-$), a nitrate ion ($NO_3^-$), a sulfate ion ($SO_4^{2-}$), a phosphate ion ($PO_4^{2-}$), a borate ion ($BO_3^{3-}$), and a hydrogen carbonate ion ($HCO_3^-$). In order to reduce an electrical resistance of the electrolytic solution, it is preferable to use, as the anode solution and the cathode solution, an alkaline solution in which an electrolyte such as a potassium hydroxide or a sodium hydroxide is dissolved in high concentration.

For the cathode solution, it is also possible to use an ionic liquid which is made of salts of cations such as imidazolium ions or pyridinium ions and anions such as $BF_4^-$ or $PF_6^-$ and which is in a liquid state in a wide temperature range, or its aqueous solution. As another cathode solution, there can be cited an amine solution of ethanolamine, imidazole, pyridine, or the like, or an aqueous solution thereof. As amine, any of primary amine, secondary amine, and tertiary amine is applicable.

To the anode flow path 12 of the anode part 10, the anode solution is supplied from the anode solution supply system 100. The anode solution supply system 100 circulates the anode solution so that the anode solution flows through inside the anode flow path 12. The anode solution supply system 100 has a pressure controller 101, an anode solution tank 102, a flow rate controller (pump) 103, a reference electrode 104, and a pressure gauge 105, and is configured to make the anode solution circulate in the anode flow path 12. The anode solution tank 102 is connected to a not-illustrated gas component collection unit which collects a gas component such as oxygen ($O_2$) contained in the circulating anode solution. The anode solution is introduced into the anode flow path 12 after a flow rate and a pressure thereof are controlled in the pressure controller 101 and the flow rate controller 103.

To the cathode flow path 21 of the cathode part 20, the cathode solution is supplied from the cathode solution supply system 200. The cathode solution supply system 200 circulates the cathode solution so that the cathode solution flows through inside the cathode flow path 21. The cathode solution supply system 200 has a pressure controller 201, a cathode solution tank 202, a flow rate controller (pump) 203, a reference electrode 204, and a pressure gauge 205, and is configured to make the cathode solution circulate in the cathode flow path 21. The cathode solution tank 202 is connected to a gas component collection unit 206 which collects a gas component such as carbon monoxide (CO) contained in the circulating cathode solution. The cathode solution is introduced into the cathode flow path 21 after a flow rate and a pressure thereof are controlled in the pressure controller 201 and the flow rate controller 203.

To the cathode flow path 23, the $CO_2$ gas is supplied from the gas supply system 300. The gas supply system 300 has a $CO_2$ gas cylinder 301, a flow rate controller 302, a pressure gauge 303, and a pressure controller 304. The $CO_2$ gas is introduced into the cathode flow path 23 after a flow rate and a pressure thereof are controlled in the flow rate controller 302 and the pressure controller 304. The gas supply system 300 is connected to the product collection system 400 which collects a product in the gas flowed through the cathode flow path 23. The product collection system 400 has a gas/liquid separation unit 401 and a product collection unit 402. A reduction product such as CO or $H_2$ contained in the gas flowed through the cathode flow path 23 is accumulated in the product collection unit 402 via the gas/liquid separation unit 401.

The anode solution and the cathode solution circulate in the anode flow path 12 and the cathode flow path 21 at a time of an electrolytic reaction operation, as described above. At a time of a refresh operation of the electrolysis cell 2 to be described later, the anode solution and the cathode solution are discharged to the waste solution collection system 600 so that the anode 11, the anode flow path 12, the cathode 22, the cathode flow path 21, and the like are exposed from the anode solution and the cathode solution. The waste solution collection system 600 has a waste solution collection tank 601 connected to the anode flow path 12 and the cathode flow path 21. Waste solutions of the anode solution and the cathode solution are collected in the waste solution collection tank 601 by opening and closing not-illustrated valves. The opening and closing of the valves, or the like is controlled collectively by the control system 500. The waste solution collection tank 601 also functions as a collection unit of a rinse solution supplied from the refresh material source 700. Further, a gaseous substance supplied from the refresh material source 700 and containing a part of a liquid substance, is also collected by the waste solution collection tank 601 according to need.

The refresh material source 700 includes a gaseous substance supply system 710 and a rinse solution supply system 720. Note that the rinse solution supply system 720 can be omitted according to circumstances. The gaseous substance supply system 710 has a gas tank 711 to be a source of a gaseous substance such as air, carbon dioxide, oxygen, nitrogen, or argon, and a pressure controller 712 which controls a supply pressure of the gaseous substance. The rinse solution supply system 720 has a rinse solution tank 721 to be a source of a rinse solution such as water and a flow rate controller (pump) 722 which controls a supply flow rate or the like of the rinse solution. The gaseous substance supply system 710 and the rinse solution supply system 720 are connected to the anode flow path 12, the cathode flow path 21, and the cathode flow path 23 via pipes. The gaseous substance and the rinse solution are supplied to each of the flow paths 12, 21, and 23 by opening and closing not-illustrated valves. The opening and closing of the valves, or the like is controlled collectively by the control system 500.

The electrolytic device 1 further includes a sensor 71 and a sensor 72. The sensor 71 acquires data indicating a discharge amount per unit time of a liquid containing water that is discharged from the anode flow path 12. As the aforementioned liquid, there can be cited a discharge solution of the anode solution, the rinse solution, and the like, for example. The sensor 72 acquires data indicating a discharge amount per unit time of a liquid containing water that is discharged from the cathode flow path 23. As the aforementioned liquid, there can be cited a discharge solution of the anode solution, the rinse solution, and the like, for example. Note that it is only required to provide at least one of the sensor 71 and the sensor 72.

As the sensor 71, a liquid level sensor can be used, for example. The liquid level sensor detects a height of a liquid surface of the liquid in the anode solution tank 102. For example, it is possible to estimate a discharge amount per unit time from a difference between a height of the liquid surface and a reference height. Note that it is also possible to design such that an anode discharge solution tank which houses a liquid discharged from the anode flow path 12 as the anode solution tank 102 and an anode solution supply tank which is connected to the anode discharge solution tank via a flow path and which houses the anode solution are provided, and data indicating the above-described discharge amount is acquired by measuring a height of the liquid housed in the anode discharge solution tank by using the liquid level sensor.

As the sensor 72, a liquid level sensor can be used, for example. The liquid level sensor detects a height of a liquid surface of the liquid in the cathode solution tank 202. For example, it is possible to estimate a discharge amount per unit time from a difference between a height of the liquid surface and a reference height. Note that it is also possible to design such that a cathode discharge solution tank which houses a liquid discharged from the cathode flow paths 21 and 23 as the cathode solution tank 202 and a cathode solution supply tank which is connected to the cathode discharge solution tank via a flow path and which houses the cathode solution are provided, and data indicating the above-described discharge amount is acquired by measuring a height of the liquid housed in the cathode solution supply tank by using the liquid sensor.

The above-described data is sent to a refresh controller 503 connected to the sensors 71 and 72, and the refresh controller 503 controls a refresh operation to be described later based on the above-described data.

A part of the reduction product accumulated in the product collection unit 402 is sent to a reduction performance detection unit 501 of the control system 500. In the reduction performance detection unit 501, a production amount and a proportion of each product such as CO or $H_2$ in the reduction product, are detected. The detected production amount and proportion of each product are input into a data collection and controller 502 of the control system 500. Further, the data collection and controller 502 collects electrical data such as a cell voltage, a cell current, a cathode potential, and an anode potential, pressures and pressure losses inside the anode flow path 12 and the cathode flow path 21 as part of a cell performance of the electrolysis cell 2, and transmits the data to the refresh controller 503.

The data collection and controller 502 is electrically connected, via bi-directional signal lines whose illustration is partially omitted, to the power controller 40, the pump 70, the pressure controller 101 and the flow rate controller 103 of the anode solution supply system 100, the pressure controller 201 and the flow rate controller 203 of the cathode solution supply system 200, the flow rate controller 302 and the pressure controller 304 of the gas supply system 300, and the pressure controller 712 and the flow rate controller 722 of the refresh material source 700, in addition to the reduction performance detection unit 501, and these are collectively controlled. Note that each pipe is provided with a not-illustrated valve, and an opening/closing operation of the valve is controlled by a signal from the data collection and controller 502. The data collection and controller 502 may also control operations of the aforementioned components at a time of an electrolysis operation, for example.

The refresh controller 503 is electrically connected, via bi-directional signal lines whose illustration is partially omitted, to the power controller 40, the flow rate controller 103 of the anode solution supply system 100, the flow rate controller 203 of the cathode solution supply system 200, the flow rate controller 302 of the gas supply system 300, and the pressure controller 712 and the flow rate controller 722 of the refresh material source 700, and these are collectively controlled. Note that each pipe is provided with a not-illustrated valve, and an opening/closing operation of the valve is controlled by a signal from the refresh controller 503. The refresh controller 503 may also control operations of the aforementioned components at a time of the electrolysis operation, for example. Further, it is also possible that the refresh controller 503 and the data collection and controller 502 are configured by one controller.

Figure 10:
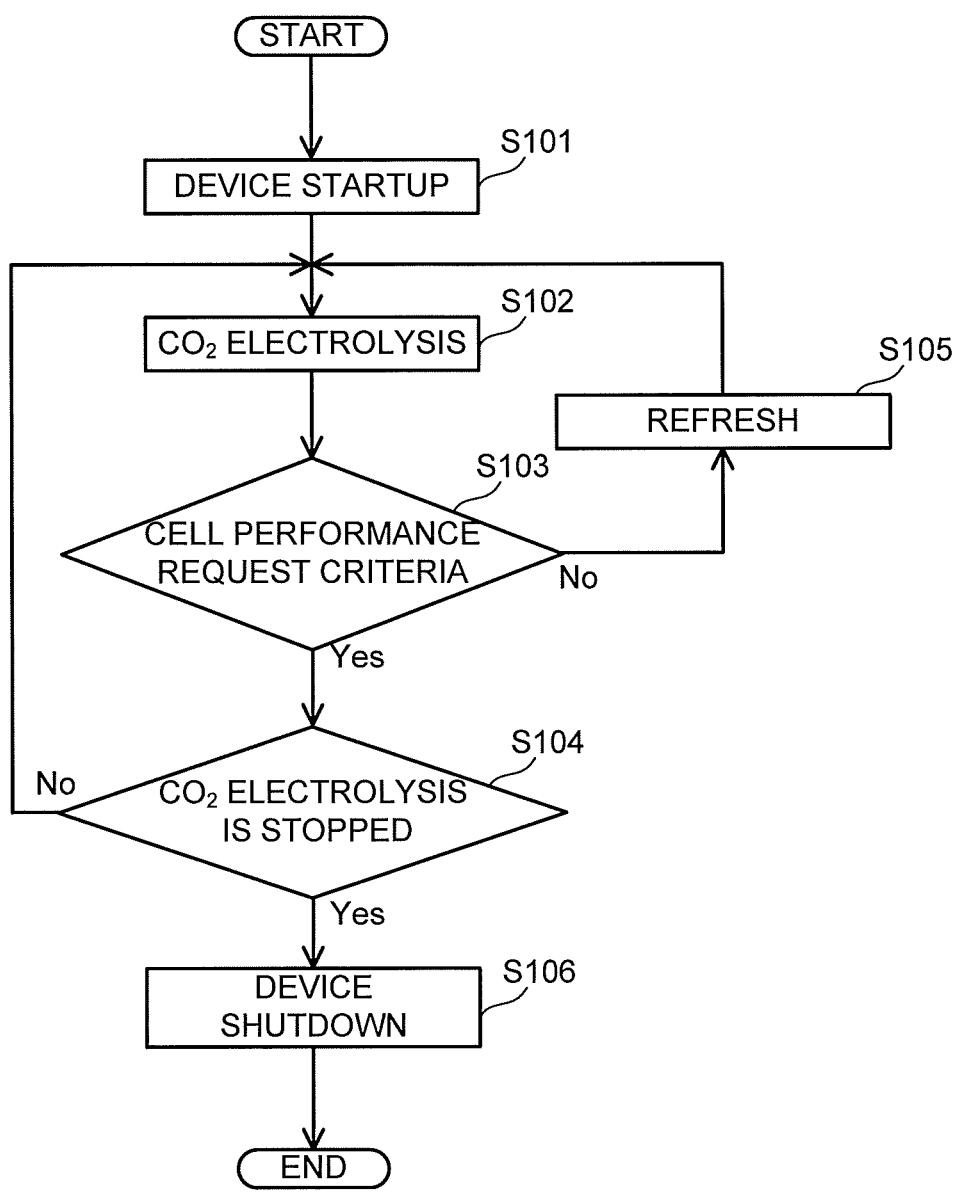
FIG. 10 is a chart illustrating an operation step of the carbon dioxide electrolytic device of the first embodiment.

A working operation of the carbon dioxide electrolytic device 1 of the embodiment will be described. First, as illustrated in FIG. 10, a start-up step S101 of the electrolytic device 1 is performed. In the start-up step S101 of the electrolytic device 1, the following operation is performed. In the anode solution supply system 100, a flow rate and a pressure are controlled by the pressure controller 101 and the flow rate controller 103, and the anode solution is introduced into the anode flow path 12. In the cathode solution supply system 200, a flow rate and a pressure are controlled by the pressure controller 201 and the flow rate controller 203, and the cathode solution is introduced into the cathode flow path 21. In the gas supply system 300, a flow rate and a pressure are controlled by the flow rate controller 302 and the pressure controller 304, and $CO_2$ gas is introduced into the cathode flow path 23.

Next, a $CO_2$ electrolysis operation step S102 is performed. In the $CO_2$ electrolysis operation step S102, application of an electrolytic voltage is started by the power controller 40 of the electrolytic device 1 after being subjected to the start-up step S101, and a current is supplied by applying the voltage between the anode 11 and the cathode 22. When the current is made to flow between the anode 11 and the cathode 22, an oxidation reaction in the vicinity of the anode 11 and a reduction reaction in the vicinity of the cathode 22 occur, which will be described below. Here, a case of producing carbon monoxide (CO) as the carbon compound is mainly described, but, the carbon compound as the reduction product of carbon dioxide is not limited to carbon monoxide, and may be other carbon compounds such as the above-described organic compounds. Further, as a reaction process caused by the electrolysis cell 2, there can be considered a case where hydrogen ions ($H^1$) are mainly produced and a case where hydroxide ions ($OH^-$) are mainly produced, but, it is not limited to either of these reaction processes.

First, the reaction process in a case of mainly oxidizing water ($H_2O$) to produce hydrogen ions ($H^+$) is described. When a current is supplied between the anode 11 and the cathode 22 from the power controller 40, an oxidation reaction of water ($H_2O$) occurs in the anode 11 which is brought into contact with the anode solution. Concretely, as presented in the following formula (1), $H_2O$ contained in the anode solution is oxidized, and oxygen ($O_2$) and hydrogen ions ($H^+$) are produced.

$$2H_2O \rightarrow 4H^1 + O_2 + 4e^- \quad (1)$$

$H^+$ produced in the anode 11 moves in the anode solution existing in the anode 11, the separator 30, and the cathode solution in the cathode flow path 21, and reaches the vicinity of the cathode 22. The reduction reaction of carbon dioxide ($CO_2$) occurs by electrons ($e^-$) based on the current supplied from the power controller 40 to the cathode 22 and $H^+$ moved to the vicinity of the cathode 22. Concretely, as presented in the following formula (2), $CO_2$ supplied from the cathode flow path 23 to the cathode 22 is reduced, and CO is produced.

$$2CO_2 + 4H^+ + 4e^- \rightarrow 2CO + 2H_2O \quad (2)$$

Next, the reaction process in a case of mainly reducing carbon dioxide ($CO_2$) to produce hydroxide ions ($OH^-$) is described. When a current is supplied between the anode 11 and the cathode 22 from the power controller 40, in the vicinity of the cathode 22, water ($H_2O$) and carbon dioxide ($CO_2$) are reduced, and carbon monoxide (CO) and hydroxide ions ($OH^-$) are produced, as presented in the following formula (3). The hydroxide ions ($OH^-$) diffuse to the vicinity of the anode 11, and as presented in the following formula (4), the hydroxide ions ($OH^-$) are oxidized, and oxygen ($O_2$) is produced.

$$2CO_2 + 2H_2O + 4e^- \rightarrow 2CO + 4OH^- \quad (3)$$

$$4OH^- \rightarrow 2H_2O + O_2 + 4e^- \quad (4)$$

In the above-described reaction processes in the cathode 22, the reduction reaction of $CO_2$ is considered to occur in the vicinity of the boundary between the gas diffusion layer 22A and the cathode catalyst layer 22B, as described above. At this time, the cathode solution which flows through the cathode flow path 21 enters up to the gas diffusion layer 22A or the cathode catalyst layer 22B has excess water, which causes a trouble such that the production amount of CO obtained by the reduction reaction of $CO_2$ reduces or the cell voltage increases. The reduction in the cell performance of the electrolysis cell 2 as above is also caused by not only deviation of distribution of ions and residual gas in the vicinity of the anode 11 and the cathode 22, the excess water in the cathode catalyst layer 22B, and precipitation of an electrolyte in the cathode 22 and the anode 11, but also precipitation of an electrolyte in the anode flow path 12 and the cathode flow path 21, and the like.

Further, there is a case where the electrolysis operation causes precipitation of salts in the cathode flow path 21 or the gas diffusion layer 22A, which blocks the flow path or reduces the gas diffusibility, resulting in that the cell performance reduces. This is because ions move between the anode 11 and the cathode 22 via the separator 30 or the ion exchange membrane, and the ions react with the gas component. For example, when a potassium hydroxide solution is used as the anode solution, and carbon dioxide gas is used as the cathode gas, potassium ions move from the anode 11 to the cathode 22, and the ions react with carbon dioxide to produce salts of potassium bicarbonate, potassium carbonate, or the like. In the cathode flow path 21 or the gas diffusion layer 22A, when an amount of the salts is equal to or less than the solubility, the salts precipitate in the cathode flow path 21 or the gas diffusion layer 22A. When the flow path is blocked, a uniform gas flow in the entire cell is prevented, and the cell performance lowers. In particular, when a plurality of cathode flow paths 21 are provided, the cell performance significantly lowers. Note that there is a case where the performance of the cell itself is improved by partial increase in the gas flow rate and the like. This is because since a gas pressure is increased, the gas component or the like supplied to the catalyst increases or the gas diffusibility increases, which improves the cell performance. In order to detect the reduction in the cell performance as above, a step S103 which determines whether or not the cell performance satisfies the request criteria, is performed.

The data collection and controller 502 collects the production amount and the proportion of each product and the cell performance such as the cell voltage, the cell current, the cathode potential, the anode potential, the pressure inside the anode flow path 12, the pressure inside the cathode flow path 21 in the electrolysis cell 2 regularly or continuously, for example, as described above. Further, in the data collection and controller 502, the request criteria of the cell performance are previously set, and it is determined whether or not collected data satisfies the set request criteria. When the collected data satisfies the set request criteria, the $CO_2$ electrolysis operation S102 is continued without performing a $CO_2$ electrolysis stop (S104). When the collected data does not satisfy the set request criteria, a refresh operation step S105 is performed.

The cell performance collected by the data collection and controller 502 is defined by parameters such as an upper limit value of a cell voltage when a constant current is made to flow through the electrolysis cell 2, a lower limit value of a cell current when a constant voltage is applied to the electrolysis cell 2, and Faradaic efficiency of the carbon compound produced by the reduction reaction of $CO_2$. Here, the Faradaic efficiency is defined as a proportion of a current contributing to production of an intended carbon compound with respect to an entire current flowed through the electrolysis cell 2. In order to maintain electrolysis efficiency, the refresh operation step S105 may be performed when the upper limit value of the cell voltage when the constant current is made to flow reaches 150% or more, preferably 120% or more of a set value. Further, the refresh operation step S105 may be performed when the lower limit value of the cell current at a time of applying the constant voltage reaches 50% or less, preferably 80% or less of a set value. In order to maintain a production amount of the reduction product such as the carbon compound, the refresh operation step S105 may be performed when the Faradaic efficiency of the carbon compound becomes 50% or less, preferably 80% or less of a set value.

Regarding the determination of the cell performance, for example, when at least one parameter of the cell voltage, the cell current, the Faradaic efficiency of the carbon compound, the pressure inside the anode flow path 12, and the pressure inside the cathode flow path 21 does not satisfy the request criteria, it is determined that the cell performance does not satisfy the request criteria, and the refresh operation step S105 is carried out. Further, it is also possible to set the request criteria of the cell performance by combining two or more of the aforementioned parameters. For example, it is also possible to perform the refresh operation step S105 when neither the cell voltage nor the Faradaic efficiency of the carbon compound satisfies the request criteria. The refresh operation step S105 is performed when at least one of the cell performance does not satisfy the request criteria. In order to stably perform the $CO_2$ electrolysis operation step S102, the refresh operation step S105 is preferably performed at an interval of one hour or more, for example.

If the request criteria of the cell performance are judged based on only any of the cell voltage, the cell current, and the Faradaic efficiency of the carbon compound, when, even in a case where the cell performance improves or does not change, salts precipitate in the flow path or the gas diffusion layer to reduce the output, it is sometimes judged that the refresh is required. In the electrolytic device, it is important to suspect the reduction in the cell performance beforehand, and to perform the refresh operation at an optimum timing.

The judgment regarding the necessity of the refresh operation is made based on not only the cell voltage, the current value, and the sensing of salts based on a voltage change in the cell, but also the performance of gas/liquid separation between the anode 11 and the cathode 22 when the anode 11 and the cathode 22 are separated by the separator 30, namely, a movement amount of the liquid or the gas between the anode 11 and the cathode 22, an amount of the product, a voltage difference relative to a reference electrode, an estimated value of the Faradaic efficiency from these parameters, and the like. The Faradaic efficiency from the respective parameter values and the necessity of the refresh operation can be comprehensively determined as judgment of the necessity of the refresh operation also from parameters to be described later, and any combination of respective values and any calculation method are applicable.

It is also possible to judge the necessity of the refresh operation based on a flooding degree estimated from respective pieces of cell data, a voltage change, and the like based on an operating method for detecting a flooding performance. Further, it is also possible to take an operating time of the electrolysis cell 2 into consideration. The operating time is not limited to an operating time after the operation is started, but may be an integrated value of the operating time so far, a duration, an operating time after the refresh operation, a calculated value of multiplication between the integrated voltage value and time, or between the current value and the time, or the like, and any combination and calculation method thereof can be applied. Further, the calculated values of these combinations are preferable when compared to the judgment based on simply the duration or the like, since a difference caused by the operating method of the electrolysis cell 2 is taken into consideration. Furthermore, it is also possible to use a variation value of the current or the voltage, a pH value and a change value of the electrolytic solution, oxygen generation amount and variation amount.

It is preferable that the operation of judging the necessity of the refresh operation is performed, and the judgment is made based on the parameter such as a cell voltage at a time of the operation, since it is possible to correctly judge the necessity of the refresh operation, although the working operation time is reduced. Note that a judgment time of the necessity of the refresh operation in this case is preferably at least half a refresh operation time, more preferably ¼ or less of the refresh operation time, and ideally ¹⁄₁₀ or less of the refresh operation time. Further, regarding the respective parameters for judging the necessity of the refresh operation, respective pieces of data of the electrolysis cell 2 are collected via an electronic network, required parameters are derived by the data collection and controllers 502 and analysis units 504 of a plurality of cells, through big data analysis, and analysis of machine learning or the like, the refresh controller 503 is made to update the request criteria of the cell performance defined by the respective parameters for judging the necessity of refresh, and in a manner as above, it is possible to constantly perform the best refresh operation.

Figure 11:
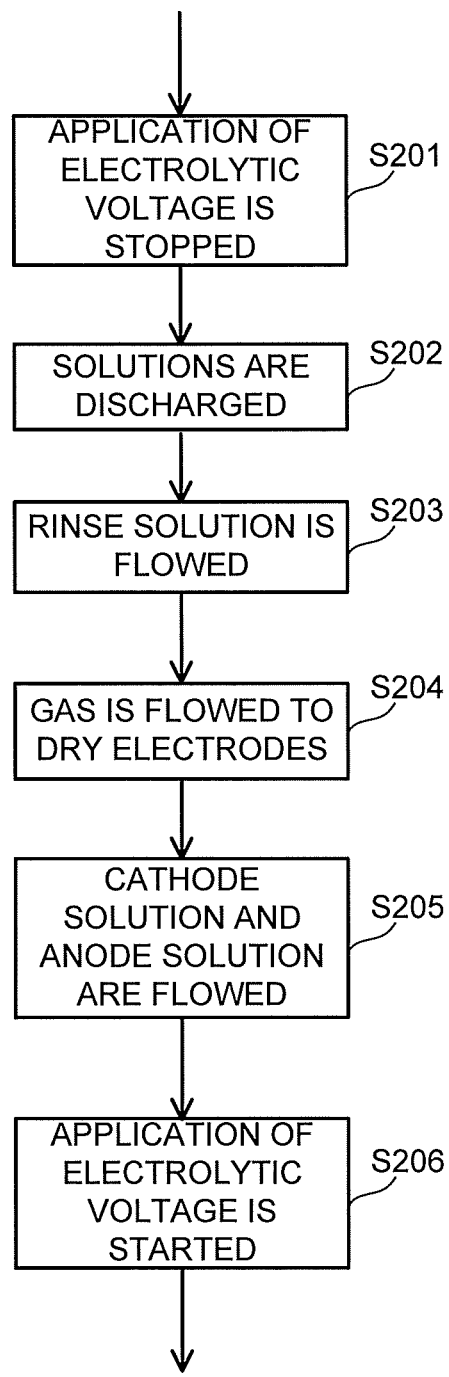
FIG. 11 is a chart illustrating a refresh step of the carbon dioxide electrolytic device of the first embodiment.

The refresh operation step S105 is performed according to a flow chart illustrated in FIG. 11, for example. First, the application of the electrolytic voltage performed by the power controller 40 is stopped, to thereby stop the reduction reaction of $CO_2$ (S201). At this time, the application of the electrolytic voltage does not necessarily have to be stopped. Next, the cathode solution and the anode solution are discharged from the cathode flow path 21 and the anode flow path 12 (S202). Next, the rinse solution is supplied to the cathode flow path 21 and the anode flow path 12 (S203), to thereby perform washing.

While the rinse solution is supplied, a refresh voltage is applied between the anode 11 and the cathode 22. This makes it possible to remove ions and impurities adhered to the cathode catalyst layer 22B. When the refresh voltage is applied so as to perform mainly oxidation treatment, ions and impurities such as organic matters adhered to the surface of the catalyst are oxidized to be removed. Further, by performing this treatment in the rinse solution, it is possible to perform not only the refresh of the catalyst but also removal of ions substituted in an ion-exchange resin at a time of using the ion exchange membrane as the separator 30.

The refresh voltage is preferably not less than −2.5 V nor more than 2.5 V, for example. Since energy is used for the refresh operation, the range of the refresh voltage is preferably as narrow as possible, and the range is more preferably not less than −1.5 V nor more than 1.5 V, for example. The refresh voltage may be cyclically applied so that the oxidation treatment of the ions and the impurities and the reduction treatment are alternately performed. This makes it possible to accelerate regeneration of the ion-exchange resin and regeneration of the catalyst. Further, it is also possible to perform the refresh operation by applying, as the refresh voltage, a voltage whose value is equal to that of the electrolytic voltage at a time of the electrolysis operation. In this case, it is possible to simplify the configuration of the power controller 40.

Next, gas is supplied to the cathode flow path 21 and the anode flow path 12 (S204), to thereby dry the cathode 22 and the anode 11. When the rinse solution is supplied to the cathode flow path 21 and the anode flow path 12, a saturation degree of water in the gas diffusion layer 22A increases, and output reduction occurs due to the diffusibility of gas. By supplying the gas, the saturation degree of water lowers, so that the cell performance is recovered, and the refresh effect is increased. The gas is preferably supplied right after the rinse solution is made to flow, and is preferably supplied at least within five minutes after the finish of supply of the rinse solution. This is because the output reduction is large due to the increase in the saturation degree of water, and if it is assumed that the refresh operation is performed at intervals of an hour, for example, an output during the refresh operation in five minutes is 0 V or significantly small, so that 5/60 of the output is sometimes lost.

When the above refresh operation finishes, the cathode solution is introduced into the cathode flow path 21, the anode solution is introduced into the anode flow path 12, and $CO_2$ gas is introduced into the cathode flow path 23 (S205). Subsequently, the application of the electrolytic voltage between the anode 11 and the cathode 22 performed by the power controller 40 is resumed, to thereby resume the $CO_2$ electrolysis operation (S206). Note that when the application of the electrolytic voltage is not stopped in S201, the aforementioned resume operation is not performed. For the discharge of the cathode solution and the anode solution from each of the flow paths 12 and 21, gas may be used or the rinse solution may be used.

The supply and flow of the rinse solution (S203) are performed for the purpose of preventing precipitation of an electrolyte contained in the cathode solution and the anode solution, and washing the cathode 22, the anode 11, and each of the flow paths 12 and 21. For this reason, as the rinse solution, water is preferable, water having an electric conductivity of 1 mS/m or less is more preferable, and water having the electric conductivity of 0.1 mS/m or less is still more preferable. In order to remove a precipitate such as the electrolyte in the cathode 22, the anode 11, and the like, an acid rinse solution having a low concentration of sulfuric acid, nitric acid, hydrochloric acid, or the like may be supplied, and the electrolyte may be dissolved by using the acid rinse solution. When the acid rinse solution having a low concentration is used, a step in which the rinse solution of water is supplied is performed in a step thereafter. It is preferable to perform, right before the gas supply step, the supply step of the rinse solution of water, in order to prevent an additive contained in the rinse solution from remaining. FIG. 1 illustrates the rinse solution supply system 720 having one rinse solution tank 721, but, when a plurality of rinse solutions such as water and the acid rinse solution are used, a plurality of rinse solution tanks 721 corresponding thereto are used.

In particular, for the refresh of the ion-exchange resin, acid or alkaline rinse solution is preferable. This provides an effect of discharging cations or anions substituted in place of protons or $OH^-$ in the ion-exchange resin. For this reason, it is preferable that the acid rinse solution and the alkaline rinse solution are made to flow alternately, the rinse solution is combined with water having an electric conductivity of 1 mS/m or less, and gas is supplied between supplies of a plurality of rinse solutions so that the rinse solutions are not mixed.

As the rinse solution, water produced through a reaction may also be used. For example, when CO is produced from $CO_2$ and protons through reduction, water is generated. It is possible that the water discharged from the cathode 22 at this time is separated through gas/liquid separation, and stored in the cathode solution tank 202 to be used. If it is designed as above, there is no need to newly supply the rinse solution from the outside, which is advantageous in terms of system. Further, by changing an electric potential to increase a reaction current, and increasing an amount of water to be produced, the water may also be supplied to the cathode flow path 21. Accordingly, the tank for the produced water, and the pipe, the pump, and the like used for the rinse solution become unnecessary, which provides a configuration that is effective in terms of system. Further, it is also possible that gas containing oxygen is supplied to the cathode flow path 21 and a voltage is applied, to thereby perform water decomposition on the electrolytic solution or the rinse solution of the anode 11, and the refresh operation is performed by using water produced by the catalyst from protons or $OH^-$ ions moved to a counter electrode. For example, in a case where Nafion is used as an ion exchange membrane in an electrolysis cell in which $CO_2$ is reduced to CO by using a gold catalyst, when air is flowed through the cathode 22 and an electric potential is applied to the cell to perform water decomposition, protons moved to the cathode 22 are reacted with oxygen by the catalyst, and water is produced. The refresh operation can be performed by using the produced water. Further, it is also possible that hydrogen gas is generated by supplying gas containing no oxygen to the cathode 22 or stopping the supply of gas thereafter, and the generated hydrogen is used to perform the refresh operation to dry the cathode 22. Accordingly, it is also possible to perform the refresh operation of the catalyst by using reducing power of protons and hydrogen.

The gas used for the gas supply and the flow step S204 preferably contains at least one of air, carbon dioxide, oxygen, nitrogen, and argon. Moreover, gas having low chemical reactivity is preferably used. Form such a point, air, nitrogen, and argon are preferably used, and nitrogen and argon are more preferable. The supply of the rinse solution and gas for refresh is not limited only to the cathode flow path 21 and the anode flow path 12, and in order to wash a surface, of the cathode 22, which is brought into contact with the cathode flow path 23, the rinse solution and the gas may be supplied to the cathode flow path 23. It is effective to supply the gas to the cathode flow path 23 in order to dry the cathode 22 also from the side of the surface which is brought into contact with the cathode flow path 23.

The above is the description regarding the case where the rinse solution and gas for refresh are supplied to both the anode part 10 and the cathode part 20, but, the rinse solution and gas for refresh may be supplied to only one of the anode part 10 and the cathode part 20. For example, the Faradaic efficiency of the carbon compound varies depending on a contact region between the cathode solution and $CO_2$ in the gas diffusion layer 22A and the cathode catalyst layer 22B of the cathode 22. In such a case, only by supplying the rinse solution and gas for refresh to only the cathode part 20, the Faradaic efficiency of the carbon compound is sometimes recovered. Depending on a type of the electrolytic solutions (anode solution and cathode solution) to be used, there is sometimes a tendency that precipitation easily occurs in one of the anode part 10 and the cathode part 20. Based on such a tendency of the electrolytic device 1, the rinse solution and gas for refresh may be supplied to only one of the anode part 10 and the cathode part 20. Moreover, depending on an operating time or the like of the electrolytic device 1, the cell performance is sometimes recovered only by drying the anode 11 and the cathode 22. In such a case, it is also possible to supply only the gas for refresh to at least one of the anode part 10 and the cathode part 20. The refresh operation step S105 can be changed in various ways according to an operation condition, a tendency, and the like of the electrolytic device 1.

As described above, in the electrolytic device 1 of the first embodiment, based on whether or not the cell performance of the electrolysis cell 2 satisfies the request criteria, it is determined whether the $CO_2$ electrolysis operation step S102 is continued or the refresh operation step S105 is performed. By supplying the rinse solution and gas for refresh in the refresh operation step S105, the entry of the cathode solution into the gas diffusion layer 22A, the excess water of the cathode catalyst layer 22B, the deviation of the distribution of the ions and the residual gas in the vicinity of the anode 11 and the cathode 22, the precipitation of the electrolyte in the cathode 22, the anode 11, the anode flow path 12, and the cathode flow path 21, and the like, which become causes of reducing the cell performance, are removed. Therefore, by resuming the $CO_2$ electrolysis operation step S102 after the refresh operation step S105, the cell performance of the electrolysis cell 2 can be recovered. By repeating the $CO_2$ electrolysis operation step S102 and the refresh operation step S105 as above based on the request criteria of the cell performance, it becomes possible to maintain the $CO_2$ electrolysis performance obtained by the electrolytic device 1 for a long period of time.

When the electrolytic solution or the rinse solution is introduced into the anode flow path 12 or the cathode flow paths 21 and 23, there is a case of causing a so-called flooding phenomenon in which a liquid enters a porous portion of the anode 11 or the cathode 22 through a capillary action to form a liquid film, which blocks the porous portion. It is difficult to detect the flooding, and in order to examine a generation amount of hydrogen, for example, it is required to perform analysis in a gas chromatograph and the like regarding the generated gas component. A result of adding a degree of progress of flooding caused by making a liquid flow through a flow path every time the precipitation of salts occurs and a degree of progress of flooding caused by the reaction, is different from a degree of precipitation of salts, so that it is not always preferable to simultaneously perform introduction of the gaseous substance for eliminating the precipitation of salts. Further, there are few indices for changing the introduction amount of the gaseous substance for preventing the flooding.

When the degree of flooding is detected in a simple manner and in accordance with that, an amount and a time of introducing gas are changed, or only the refresh operation for introducing the gas to perform drying is performed separately from the precipitation of salts, it becomes possible to efficiently operate the electrolysis cell 2.

As a method of detecting the presence/absence of the flooding in a simple manner, there is a method of detecting an amount of water which moves from the anode 11 to the cathode 22. An increase in the movement amount indicates progress of the flooding. In the electrolytic device of the embodiment, at least one sensor of the sensor 71 and the sensor 72 is used to detect a discharge amount of a liquid containing water which is discharged from the anode flow path 12 or the cathode flow paths 21 and 23, and the above-described movement amount is calculated based on the above-described discharge amount, to thereby detect the presence/absence of the flooding. Since there is a correlation between the amount of water which moves from the anode 11 to the cathode 22 when the cell operation is stopped and the flooding, it is possible to detect the flooding by measuring this movement amount, and by introducing the gas into the cathode to perform drying processing, it is possible to recover the efficiency of the cell to perform the efficient operation.

For example, when there are provided a tank which houses a liquid discharged from the cathode flow path 23 (cathode solution tank 202), and the sensor 71, it is possible to measure the amount of water moved from the anode 11 to the cathode 22. There is a case where water is produced by a reaction in the cathode at this time, and by subtracting an amount of the water from an amount of water stored in the cathode solution tank 202, it is possible to measure the movement amount. From viewpoints of cost and size, the cathode solution tank 202 preferably uses a gas/liquid separation layer which separates a cathode discharge solution and cathode discharge gas, since the number of parts is reduced. When a reduction product in the cathode part 20 is a liquid, it becomes difficult to determine a movement amount of water from an amount of liquid discharged from the cathode 22, so that a cathode reaction in which a reaction occurs at a stable component ratio is preferable.

Under a condition where the reduction in performance by normal flooding does not occur, a ratio of a movement amount of water with respect to an electric charge amount (Coulomb amount) applied to the electrolysis cell 2 is constant. However, when the performance is reduced by the flooding, the ratio of the movement amount is changed, and the amount of water which moves from the anode 11 to the cathode 22 increases.

For example, when a case where a movement amount of water with respect to a Coulomb amount is 1:1, namely, one molecule of water moves with respect to one electron is considered, it can be judged that the flooding occurs in a stage where the ratio exceeds 1:1.1. This ratio indicates a constant value in a range of about 1: –0.5 to 1:6, but, it is arbitrary. When this increment exceeds 1: an arbitrary value of cell (reference value) plus at least 0.1, a possibility of the flooding is very high. It can be said that the possibility of the flooding is high in a stage where the increment exceeds the arbitrary value of the cell plus 0.02, more preferably.

In order to prevent the reduction in performance caused by the flooding beforehand, by detecting, based on a movement amount of water, a stage before the reduction in performance occurs or a stage where at least the reduction in performance starts to occur, stopping the electrolytic operation, and making the dry gas flow through the cathode 22, it is possible to perform the refresh operation in which drying processing is performed on the cathode 22. By performing such an operation, it is possible to maintain the performance of the electrolytic device 1. Note that it is preferable to dry the cathode 22, stop the supply of the anode solution, and make the dry gas flow through the anode 11 as well so that the drying of the cathode 22 is facilitated.

The refresh operation for preventing the flooding is preferably performed in a period where the electrolytic operation is not performed. However, the stopping of the electrolytic operation leads to a reduction in efficiency depending on timings. Accordingly, it is also possible that the refresh operation for drying the cathode 22 is not performed, but the cathode 22 can be dried while performing the electrolytic operation by increasing a gas amount of the gas which is supplied to the cathode 22. It is preferable to design as above since it is possible to continue the electrolytic operation.

When the tank that houses the liquid discharged from the anode flow path 12 (anode solution tank 102) is provided, and the sensor 72 is provided, it is possible to measure an amount (discharge amount) of water that moves from the cathode 22 to the anode 11. When the water is reduced by the reaction in the anode 11, by subtracting an amount of the water from an amount of a liquid determined by the data obtained by the sensor 72, it is possible to measure an amount of water that moves from the anode 11 to the cathode 22.

In the reaction in the anode 11, the Faradaic efficiency is stabilized more often when compared to the reaction in the cathode 22, so that by using the sensor 72, it is possible to stably measure the amount of water that moves from the cathode 22 to the anode 11. When various carbon compounds are produced from carbon dioxide by changing ratios in the cathode 22, an amount of water produced by the reaction becomes different with respect to a current value. Consequently, it is difficult to correctly determine the calculated movement amount of water. It is difficult, in order to correctly determine the movement amount of water, to correctly determine amounts of a plurality of products produced in the cathode 22.

It is also possible to design such that the liquid discharged from the cathode flow path 21 and the cathode flow path 23 is returned to the anode solution tank 102 via a flow path and the pump 70. In this case, a reduction amount of liquid can be approximated as a reduction amount of water.

It is also possible to use the discharged anode solution as the rinse solution. In this case, there is a need to measure and calculate an amount of liquid used as the rinse solution, and perform calculation by adding or subtracting the calculated result from the movement amount.

By providing both of the sensor 71 and the sensor 72, it is possible to estimate the reaction component in the cathode 22, based on the change in the amount of water that moves from the anode 11 to the cathode 22. For example, when the amount of change is small, it is possible to detect that the reaction in the cathode 22 is a reaction with small production amount of water.

Between a reaction represented by a reaction formula: $CO_2+2H^+ \rightarrow CO+H_2O$ and a reaction represented by a reaction formula: $CO_2+8H^+ \rightarrow CH_4+2H_2O$, a production amount of water is different even if the same current value is employed, and it is also possible to determine the production amount of water caused by the reaction based on the current value and the movement amount of water.

Figure 12:
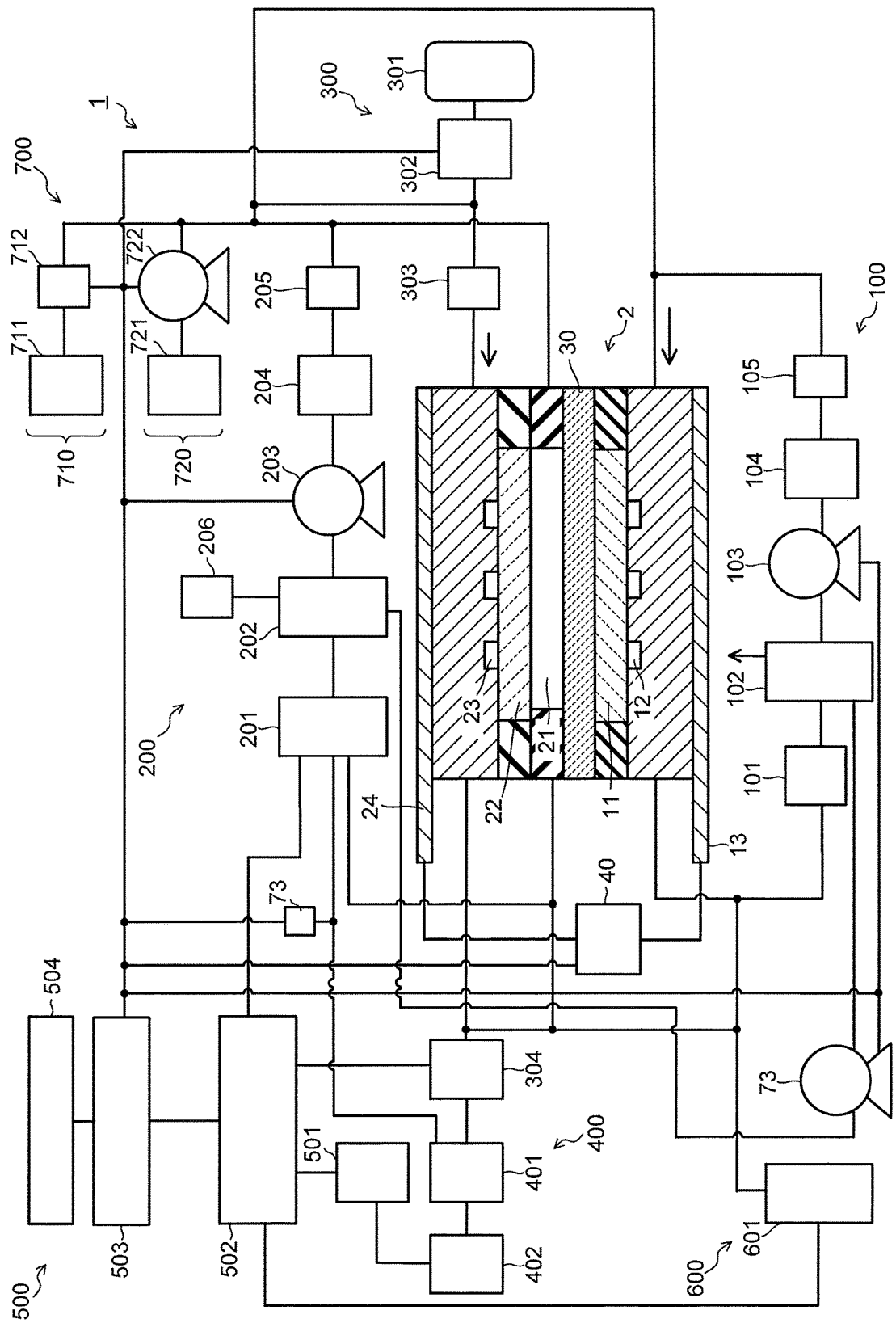
FIG. 12 is a view illustrating another example of the carbon dioxide electrolytic device of the first embodiment.

It is also possible to provide another sensor in place of the sensors 71 and 72. FIG. 12 is a view illustrating another example of the electrolytic device. An electrolytic device 1 illustrated in FIG. 12 is different from the electrolytic device 1 illustrated in FIG. 1 in a point that it has a sensor 73 in place of the sensors 71 and 72. The explanation can be appropriately cited regarding common parts.

As the sensor 73, a liquid sensor can be used, for example. The liquid sensor acquires data indicating a refractive index of light or a pressure inside a discharge flow path in which a gas/liquid two-phase flow is caused and which is connected to the cathode flow path 23. Based on the above-described data, a discharge amount per unit time can be calculated. The liquid sensor is preferable since it easily calculates a correct discharge amount in an inexpensive manner when compared to the liquid level sensor.

The data acquired by the sensor 73 is sent to the refresh controller 503 connected to the sensor 73, and the refresh controller 503 judges the presence/absence of the flooding based on the above-described data to control the refresh operation.

Figure 13:
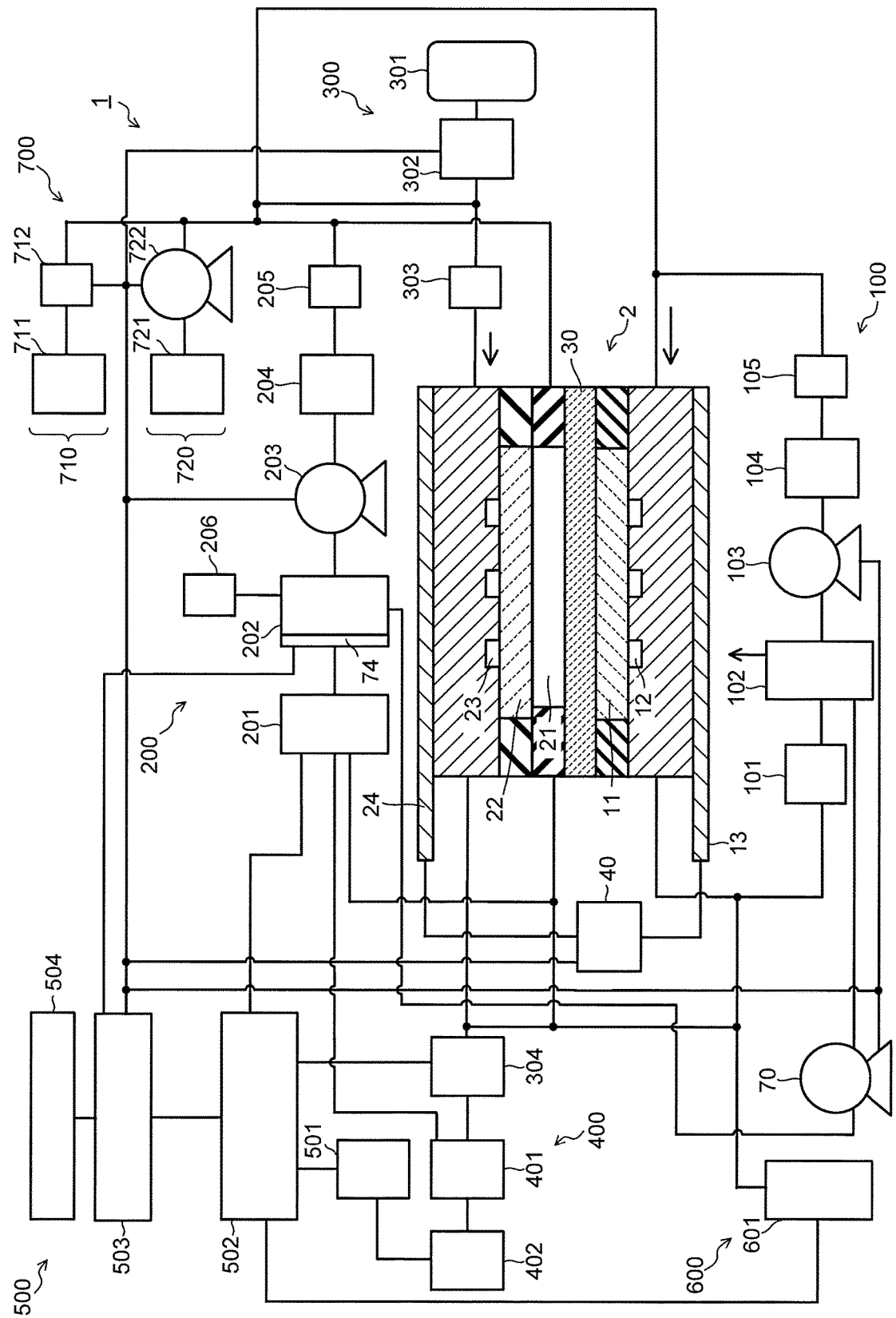
FIG. 13 is a view illustrating another example of the carbon dioxide electrolytic device of the first embodiment.

FIG. 13 is a view illustrating another example of the electrolytic device 1. An electrolytic device 1 illustrated in FIG. 13 is different from the electrolytic device 1 illustrated in FIG. 1 in a point that it has a sensor 74 in place of the sensors 71 and 72.

As the sensor 74, it is possible to use a concentration sensor, for example. The concentration sensor acquires data indicating a concentration of at least one ion selected from the group consisting of ions in the liquid in the cathode solution tank 202, for example. As the at least one kind of ion, there can be cited an ion contained in the electrolytic solution, for example.

The data acquired by the sensor 73 is sent to the refresh controller 503 connected to the sensor 73, and the refresh controller 503 judges the presence/absence of the flooding based on the above-described data to control the refresh operation.

Based on the above-described data, it is possible to know an amount of ions, per unit time, that move from the anode 11 to the cathode 22. The amount of ions, per unit time, that move from the anode 11 to the cathode 22 changes according to an operation condition of the electrolysis cell 2. The movement amount of ions can be determined from the current that is applied to the electrolysis cell 2. The movement amount of ions is in a proportional relationship with respect to the current value of the electrolysis cell 2, and can be determined by approximation. In particular, the above-described proportional relationship when using the ion exchange membrane as the separator 30 is correct.

When the movement amount of water is considered, it is possible to approximate an amount of water moved in accordance with a current value particularly when the ion exchange membrane is used as the separator 30. Further, when a porous body is used for the separator 30, ions in the anode solution are moved. Based on the above, it is possible to calculate the movement amount of water by measuring the ion concentration. When the movement amount of water becomes large with respect to the current amount, the ion concentration lowers, and thus the flooding can be detected. When the flooding is not progressed, the movement amount of water is a normal amount with respect to the current amount, and thus the change in the ion concentration is small.

It is also possible to add a reagent for detection containing an ion which is easily detectable to the electrolytic solution. As the reagent for detection, for example, there can be cited an organic molecule having a characteristic absorption in a UV or infrared region, or the like. When the ion exchange membrane is used as the separator 30, by using a large organic molecule, a movement of the reagent for detection between the anode 11 and the cathode 22 does not occur almost at all, which is preferable for the measurement of the movement amount of water. Further, it is also possible to employ an inorganic molecule which does not get involved with the reaction.

When the electrolytic operation is continued, there occurs a phenomenon that the ion concentration of the anode solution is lowered in the electrolysis cell 2 with a small movement amount of water with respect to the movement amount of ions. The cell resistance is increased by the change in the ion concentration of the anode solution particularly when the porous body is used as the separator 30. Besides, since the product in the cathode 22 is changed or the overvoltage in the anode 11 is increased by the change in concentration, the reaction efficiency is lowered. Accordingly, by connecting the cathode solution tank 202 and the anode solution tank 102 using a flow path such as a pipe and returning the liquid discharged from the cathode flow paths 21 and 23 to the anode flow path 12 via the pump 70, the ion concentration can be kept constant, resulting in that the reduction in efficiency can be suppressed.

When the movement amount of water is measured when the operation of the electrolysis cell 2 is stopped, it is not efficient in terms of system when the electrolysis cell 2 is stopped for detecting the flooding. However, the movement amount of water changes depending on the operation condition of the electrolysis cell 2. This is significant in a case of using the ion exchange membrane as the separator 30, in particular.

Accordingly, it is possible to detect the presence/absence of the flooding from an amount of ions and a movement amount of water moved from the anode 11 to the cathode 22, by combining the sensor 71 and the sensor 74, for example. If the ion is set as a monovalent ion, the movement amount of ion can be approximated to the current value which is applied to the electrolysis cell 2. Regarding the movement amount of water with respect to the movement amount of the monovalent ion determined from this current value, water with the number of moles same as the amount of ions moves when a normal ion exchange membrane is used. It is possible to detect the flooding from the movement amount of water with respect to the movement amount of the monovalent ion.

The movement amount of water with respect to the movement amount of the monovalent ion changes depending on the water repellency of the gas diffusion layer, the water repellency of the catalyst layer, the kind of separator, the gas flow rate, the component of the anode solution, and the like, and ratios thereof are arbitrary. However, it is possible to detect the change caused by the flooding, and it is possible to know that the flooding is progressed when the movement amount of water becomes larger than that in the state where no flooding occurs.

It is also possible to use the anode solution as the rinse solution. In this case, there is a need to measure and calculate an amount of liquid used as the rinse solution, and perform calculation by adding or subtracting the ion concentration. As the rinse solution, when the ion concentration of the liquid in the anode solution tank 102 is lower than that of the liquid with high ion concentration in the cathode solution tank 202, the liquid in the anode solution tank 102 is more preferable since it easily dissolves salts as the rinse solution. In the opposite case, it is preferable to use the liquid in the cathode solution tank 202. By measuring the ion concentration, it is also possible to judge the degree of precipitation of salts or the effect of the rinse solution. Further, when the sensor 74 is installed together with a liquid level sensor, it is possible to perform detailed measurement regarding the reaction situation in the cell such as the reaction situation in the cathode 22, the effect of the rinse solution, and the degree of precipitation of salts.

Figure 14:
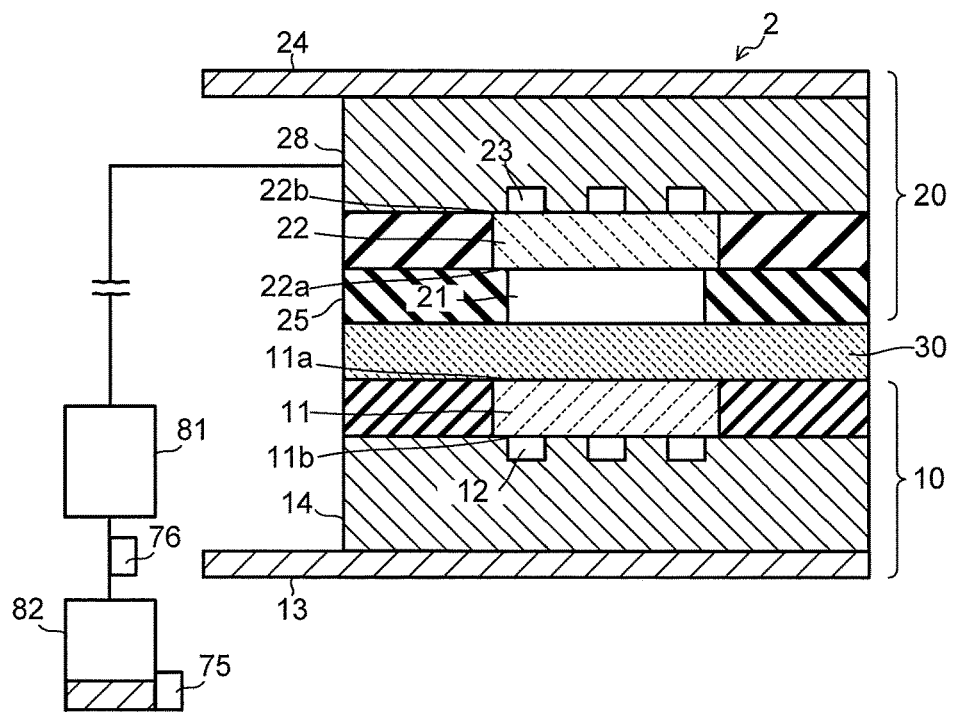
FIG. 14 is a schematic view for explaining another example of the carbon dioxide electrolytic device of the first embodiment.
Figure 15:
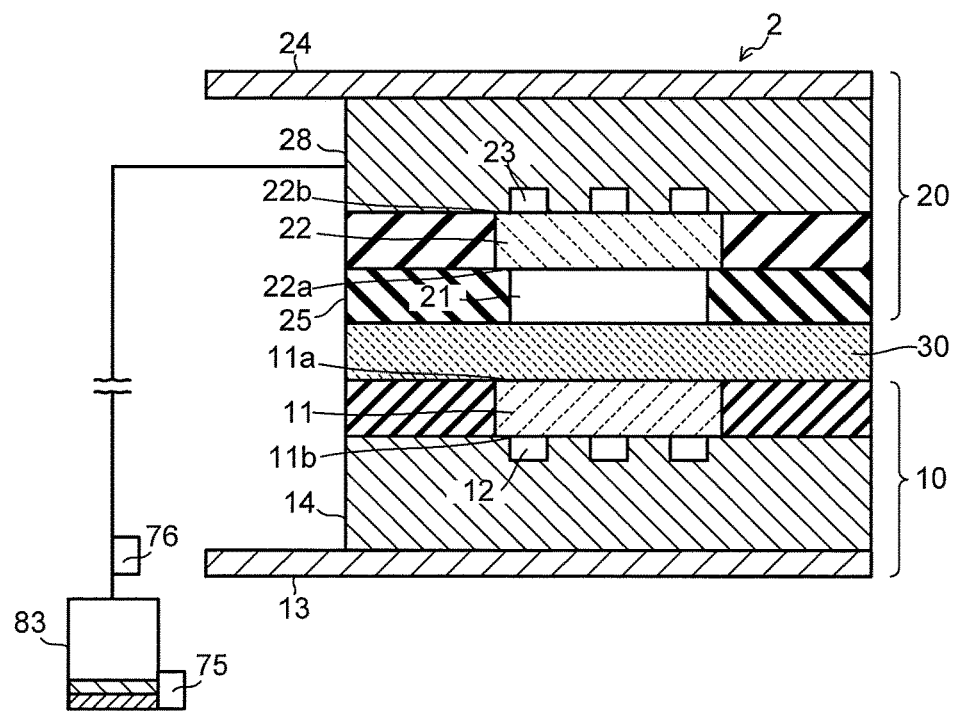
FIG. 15 is a schematic view for explaining another example of the carbon dioxide electrolytic device of the first embodiment.

It is also possible to provide a sensor to the outside of the electrolysis cell 2. Each of FIG. 14 and FIG. 15 is a schematic view for explaining another example of the electrolytic device. FIG. 14 illustrates an electrolysis cell 2, a reactor 81, a tank 82, a sensor 75, and a sensor 76. FIG. 15 illustrates an electrolysis cell 2, a reactor 83, a sensor 75, and a sensor 76. Note that it is only required to provide at least one of the sensor 75 and the sensor 76. Note that the explanation of the electrolytic device 1 illustrated in FIG. 1 can be appropriately cited.

The reactor 81 is connected to the cathode flow path 23 via the gas/liquid separation unit 401 and the product collection unit 402. The reactor 81 makes a carbon compound discharged from the cathode flow path 23 and hydrogen or water supplied from the outside react with each other to produce a carbon compound such as methanol. The carbon compound is housed in the tank 82 via a discharge flow path connected to the reactor 81. When methanol is produced, the carbon compound discharged from the cathode flow path 23 is made to react with hydrogen, and react by being heated to about 200 to 400° C. by using a Pd/ZnO catalyst or a Cu/ZnO catalyst, to thereby produce methanol.

When the carbon compound produced by reducing carbon dioxide is mixed with hydrogen and supplied to the reactor 81, it is possible to synthesize methanol. The synthesized liquid is methanol, but, water from the electrolysis cell 2 is mixed therein. Here, by providing a concentration sensor that acquires data indicating a concentration of methanol as the sensor 75, it is possible to measure a movement amount (discharge amount) of water per unit time derived from the electrolysis cell 2. By determining an amount of water moved from the anode 11 to the cathode 22 based on the measured movement amount of water, it is possible to detect the flooding.

As the sensor 75, it is also possible to use a concentration sensor that acquires data indicating a concentration of at least one ion selected from the group consisting of ions in the liquid containing the product. By comparing the concentration of ion contained in the liquid with the amount of ion determined from the current value, the amount of moved water per unit time can be measured. Further, it is also possible to provide, as the sensor 75, a liquid level sensor that acquires data indicating a height of a liquid surface of the liquid containing the product.

As the sensor 76, it is also possible to use a liquid sensor. It is also possible to acquire data indicating a refractive index of light or a pressure inside a discharge flow path by using the liquid sensor, since a synthesized amount of methanol can be checked from an amount of at least one of hydrogen and a carbon compound.

There is a crossover phenomenon in which oxygen moves from the anode 11 to the cathode 22, and the phenomenon significantly occurs particularly when the porous body is used for the separator 30. The moved oxygen reacts with the carbon compound, hydrogen, or proton in the cathode 22 to produce water. This reaction makes the carbon compound and hydrogen produced through the reduction to be oxidized again to return them to carbon dioxide or water, and thus the efficiency of the electrolysis cell 2 is reduced. Further, there is also produced oxygen which is moved to the cathode 22 but is not oxidized again and directly moved from the cathode flow path 23. The oxygen reacts with hydrogen in the reactor 81 to produce water. A movement amount of oxygen caused by this crossover phenomenon can be determined from the current value of the electrolysis cell 2, an amount of produced water, and the like. In order to correctly measure the movement amount of oxygen, it is preferable that an amount (discharge amount) of liquid discharged from the cathode flow path 23 and the reactor 81 can be measured, and thus it is preferable to provide sensors capable of measuring the discharge amount of liquid to both of the cathode flow path 23 and the reactor 81. This makes it possible to determine an amount of oxygen discharged from the cathode flow path 23 based on a difference between an amount of liquid discharged from the cathode flow path 23 and an amount of liquid discharged from the reactor 81.

In addition, it is also possible to provide a sensor to the device after performing a separation step in which methanol is synthesized and then is separated from an impurity such as water. Accordingly, the sensor can be used as a sensor that measures selectivity, a reaction efficiency, and the like of the reactor 81. By returning the separated water to the anode flow path 12, it is also possible to suppress the reduction in the ion concentration of the anode solution.

Note that although the example of synthesizing methanol using the reactor 81 has been described, the product in the reactor 81 is not limited to methanol and is arbitrary. For example, it is also possible to produce methane, ethanol, acetone, acetic acid, formic acid, propanol, butanol, ethylene, ethane, butadiene, propadiene, and so on.

It is also possible to provide a reactor 83 as illustrated in FIG. 15, in place of the reactor 81. As the reactor 83, for example, it is possible to use not only a thermochemical reactor but also an electrochemical reactor, a bioreactor, or the like.

For example, when CO gas produced in the cathode 22 is turned into butanol in a bioreactor, the produced butanol and water are separated. Accordingly, by providing a butanol sensor, an ion concentration sensor, a liquid level sensor, or the like as the sensor 75 to the reactor 83, it is possible to measure a movement amount of water per unit time from the electrolysis cell 2. Further, it is also possible to provide a liquid sensor as the sensor 76 to acquire data indicating a refractive index of light or a pressure inside the discharge flow path. Besides, since the produced butanol and water are separated, by returning the separated water to the anode flow path 12, it is possible to suppress the reduction in the ion concentration of the anode solution.

Second Embodiment

Figure 16:
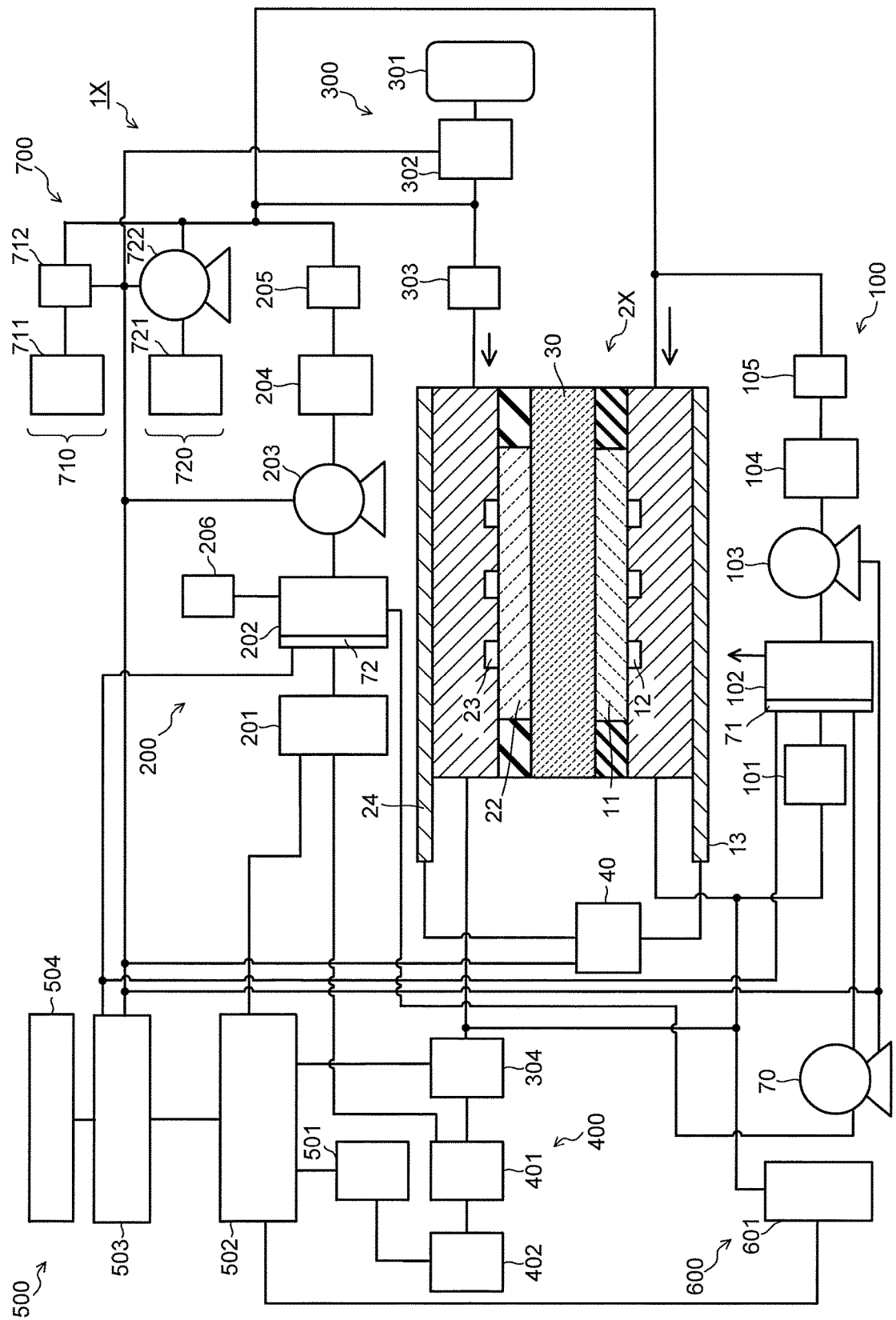
FIG. 16 is a view illustrating a carbon dioxide electrolytic device of a second embodiment.
Figure 17:
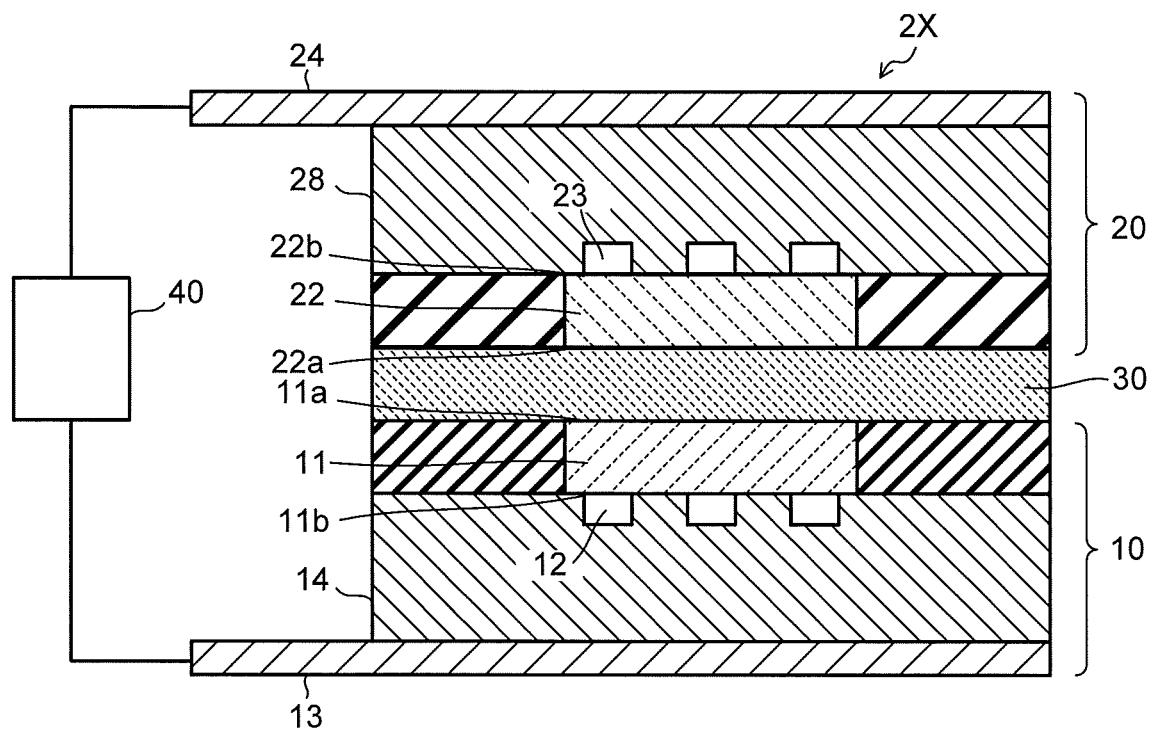
FIG. 17 is a sectional view illustrating an electrolysis cell of the carbon dioxide electrolytic device illustrated in FIG. 16.

FIG. 16 is a view illustrating a configuration of a carbon dioxide electrolytic device according to a second embodiment, and FIG. 17 is a sectional view illustrating a configuration of an electrolysis cell in the electrolytic device illustrated in FIG. 16. A carbon dioxide electrolytic device 1X illustrated in FIG. 16 includes an electrolysis cell 2X, an anode solution supply system 100 which supplies an anode solution to the electrolysis cell 2X, a gas supply system 300 which supplies carbon dioxide ($CO_2$) gas to the electrolysis cell 2X, a product collection system 400 which collects a product produced by a reduction reaction in the electrolysis cell 2X, a control system 500 which detects a type and a production amount of the collected product, and performs control of the product and control of a refresh operation, a waste solution collection system 600 which collects a waste solution of the anode solution, and a refresh material source 700 which recovers an anode, a cathode, or the like of the electrolysis cell 2X, similarly to the carbon dioxide electrolytic device 1 according to the first embodiment.

The carbon dioxide electrolytic device 1X illustrated in FIG. 16 basically includes a configuration similar to that of the electrolytic device 1 illustrated in FIG. 1, except that a configuration of the electrolysis cell 2X is different. As illustrated in FIG. 17, the electrolysis cell 2X includes an anode part 10, a cathode part 20, and a separator 30. The anode part 10 includes an anode 11, an anode flow path 12, and an anode current collector 13. The cathode part 20 includes a cathode 22, a cathode flow path 23, and a cathode current collector 24, and does not have a cathode flow path 21. A power controller 40 is connected to the anode 11 and the cathode 22 via a current introduction member. Note that a cathode solution tank 202 functions as a cathode discharge solution tank which houses a liquid containing water which is discharged from the cathode flow path 21. Note that a component required for supplying a cathode solution to the cathode flow path 21 may not be provided.

The anode 11 preferably has a first surface 11a which is brought into contact with the separator 30, and a second surface 11b which faces the anode flow path 12. The first surface 11a of the anode 11 is brought into close contact with the separator 30. The anode flow path 12 is formed of a pit (groove portion/concave portion) provided in a flow path plate 14. The anode solution flows through inside the anode flow path 12 so as to be brought into contact with the anode 11. The anode current collector 13 is electrically brought into contact with a surface on a side opposite to the anode 11 of the flow path plate 14 which forms the anode flow path 12. The cathode 22 has a first surface 22a which is brought into contact with the separator 30, and a second surface 22b which faces the cathode flow path 23. The cathode flow path 23 is formed of a pit (groove portion/concave portion) provided in a flow path plate 28. The cathode current collector 24 is electrically brought into contact with a surface on a side opposite to the cathode 22 of the flow path plate 28 which forms the cathode flow path 23.

A gaseous substance supply system 710 and a rinse solution supply system 720 of the refresh material source 700 are connected to the anode flow path 12 and the cathode flow path 23 via pipes. The anode flow path 12 and the cathode flow path 23 are connected to the waste solution collection system 600 via pipes. A rinse solution discharged from the anode flow path 12 and the $CO_2$ gas flow path is recovered into a waste solution collection tank 601 of the waste solution collection system 600. Gas for refresh discharged from the anode flow path 12 and the $CO_2$ gas flow path is recovered into a not-illustrated waste gas collection tank via the waste solution collection system 600 or released into the atmosphere. Composing materials and the like of the respective parts are similar to those of the electrolytic device 1 of the first embodiment, and details thereof are as described above.

In the electrolytic device 1X of the second embodiment, a start-up step S101 of the electrolytic device 1X and a $CO_2$ electrolysis operation step S102 are performed in a similar manner to the electrolytic device 1 of the first embodiment, except that supply of a cathode solution is not performed. Note that a reduction reaction of $CO_2$ in the cathode 22 is performed by $CO_2$ supplied from the cathode flow path 23 and the anode solution permeated the cathode 22 via the separator 30. When it is determined that the cell performance does not satisfy the request criteria, a refresh operation step S105 is performed. In the electrolytic device 1X of the second embodiment, the refresh operation step S105 is performed as follows.

First, a $CO_2$ reduction reaction is stopped. At this time, application of an electrolytic voltage performed by the power controller 40 may be maintained or stopped. Next, the anode solution is discharged from the anode flow path 12. Next, a rinse solution is supplied from the rinse solution supply system 720 to the anode flow path 12 and the cathode flow path 23, to thereby wash the anode 11 and the cathode 22. While the rinse solution is supplied, a refresh voltage may be applied between the anode 11 and the cathode 22, in a similar manner to the first embodiment. Next, gas is supplied from the gaseous substance supply system 710 to the anode flow path 12 and the cathode flow path 23, to thereby dry the anode 11 and the cathode 22. The gas and the rinse solution used for the refresh operation step are similar to those in the first embodiment. When the above refresh operation finishes, the anode solution is introduced into the anode flow path 12, and $CO_2$ gas is introduced into the cathode flow path 23. Subsequently, the $CO_2$ electrolysis operation is resumed. When the application of the electrolytic voltage performed by the power controller 40 is stopped, the application is resumed.

Also in the electrolytic device 1X of the second embodiment, based on whether or not the cell performance of the electrolysis cell 2X satisfies the request criteria, it is determined whether the $CO_2$ electrolysis operation is continued or the refresh operation is performed. By supplying the rinse solution and the gas in the refresh operation step, deviation of distribution of ions in the vicinity of the anode 11 and the cathode 22, which become a cause of reducing the cell performance, is eliminated, and further, excess water in the cathode 22, the precipitation of the electrolyte in the anode 11 and the cathode 22, blocking of the flow path caused by the precipitation of the electrolyte, and the like are removed. Therefore, by resuming the $CO_2$ electrolysis operation after the refresh operation step, the cell performance of the electrolysis cell 2X can be recovered. By repeating the $CO_2$ electrolysis operation and the refresh operation as above based on the request criteria of the cell performance, it becomes possible to maintain the $CO_2$ electrolysis performance obtained by the electrolytic device 1X for a long period of time.

When liquid passes through the separator 30 at a relatively low pressure, for example, a hydrophilic polytetrafluoroethylene (PTFE) porous body or the like is used, the rinse solution is supplied to only the anode flow path 12, and a pressure is applied to the liquid at an anode outlet by using a not-illustrated valve or the like or the anode outlet is blocked. Accordingly, the rinse solution passes through the separator 30, flows into the cathode 22, and the rinse solution flows out from a discharge port of the cathode 22. This makes it possible to perform the refresh of the cathode 22 and the refresh of the anode 11 at the same time. This configuration eliminates the necessity of the device which makes the rinse solution flow through the cathode 22, so that the device becomes compact in size, and further, the system is simplified, which is preferable.

Note that a pipe through which air gas is introduced into the cathode 22 may be connected to the cathode 22. At a time of the refresh, it is possible that gas containing air is supplied to the cathode 22, and a refresh voltage is applied between the anode 11 and the cathode 22, to thereby cause a water electrolysis reaction. On the anode 11 side, oxygen is generated by an oxidation catalyst, and generated protons move to the cathode 22 through the separator 30 or an electrolyte membrane. In the cathode 22, the protons and oxygen in the air are reacted by a cathode catalyst, resulting in that water is produced. By using the produced water, salts in the cathode can be dissolved to be discharged. Further, the produced water is pure water, so that it can be used to wash the cathode 22. At this time, impurities in the cathode 22 can be subjected to reduction treatment by using the protons moved to the cathode 22, and it is possible to regenerate the catalyst and the members. This configuration eliminates the necessity of the device which supplies the rinse solution to the cathode 22, so that the device becomes compact in size, and further, the system is simplified, which is preferable. Further, when, before the flow of the $CO_2$ gas to be performed thereafter, the air flowed through the cathode is stopped, the generated protons react with each other to generate hydrogen, which enables to push out generated water. When the oxygen-containing gas is stopped before performing push with $CO_2$, a regeneration function of the catalyst and the members provided by the protons becomes more effective. This is because other catalysts which are difficult to be reduced and the respective members of the cathode 22 are reduced, due to the absence of oxygen. Concretely, there can be cited organic matters of impurities, metal oxides, and the like. When $CO_2$ is supplied thereafter to cause a reaction, it is possible to further expect a refresh effect.

Further, also in the electrolytic device 1X of the second embodiment, the refresh controller 503 judges the presence/absence of the flooding based on the data from the sensors 71 and 72, to thereby control the refresh operation. Note that it is also possible to provide the sensor 73 or the sensor 74 in place of the sensors 71 and 72, similarly to the first embodiment. This makes it possible to control the necessity of the refresh operation in accordance with the presence/absence of the flooding.

EXAMPLES

Example 1

An electrolytic device illustrated in FIG. 1 was fabricated, and an electrolysis performance of carbon dioxide was examined. First, on a carbon paper provided with a porous layer, a cathode to which carbon particles on which gold nanoparticles were supported were applied, was produced by the following procedure. A coating solution in which the carbon particles on which the gold nanoparticles were supported, pure water, a Nafion solution, and ethylene glycol were mixed was produced. An average particle diameter of the gold nanoparticles was 3 nm, and a supported amount thereof was 10 mass %. The coating solution was filled in an air brush, and spray-coated on the carbon paper provided with the porous layer, by using Ar gas. After the coating, washing was performed by flowing pure water for 30 minutes, and thereafter, the organic matter such as ethylene glycol was oxidized to be removed through immersion in a hydrogen peroxide solution. This was cut into a size of 2×2 cm to be set as the cathode. Note that a coating amount of Au was estimated as about 0.4 mg/cm$^2$ from a mixing amount of the gold nanoparticles and the carbon particles in the coating solution. For an anode, an electrode in which $IrO_2$ nanoparticles to be a catalyst were applied to Ti mesh was used. As the anode, one in which $IrO_2$/Ti mesh was cut into 2×2 cm was used.

As illustrated in FIG. 2, the electrolysis cell 2 was produced in a manner that the cathode current collector 24, the cathode flow path 23 (the flow path plate 28), the cathode 22, the cathode flow path 21 (the flow path plate 25), the separator 30, the anode 11, and the anode flow path 12 (the anode current collector 13) were stacked in this order from the top, the stack was sandwiched by the not-illustrated support plates, and tightened by bolts. For the separator 30, a Nafion film was used. The $IrO_2$/Ti mesh of the anode 11 was brought into close contact with the PTFE porous body. A thickness of the cathode flow path 21 was set to 0.5 mm. Note that an evaluation temperature was set to room temperature.

The electrolytic device 1 illustrated in FIG. 1 was fabricated using the above-described electrolysis cell 2, and the electrolytic device was operated under the following condition. $CO_2$ gas was supplied to the cathode flow path 21 at 60 sccm, and a liquid trap was provided to an outlet of the cathode flow path 21. An aqueous potassium bicarbonate solution (concentration 1 M $KHCO_3$) of 300 mL was introduced into the anode flow path 12 at a flow rate of 2 mL/min. Next, by controlling a voltage with the use of the power controller 40, a constant current of 400 mA was applied at a constant current density of 100 mA/cm$^2$ between the anode 11 and the cathode 22 to cause an electrolytic reaction of $CO_2$, and a cell voltage at that time was measured and collected by the data collection and controller. Further, a part of gas output from the cathode flow path 23 was collected, and production amounts of CO gas produced by a reduction reaction of $CO_2$ and $H_2$ gas produced by a reduction reaction of water were analyzed by a gas chromatograph. In the data collection and controller, based on the gas production amounts, a partial current density of CO or $H_2$, and Faradaic efficiency being a ratio between the entire current density and the partial current density were calculated and collected. In a similar manner, production amounts of CO or $H_2$ gas in the anode solution flow path were analyzed by a gas chromatograph.

It was designed such that pure water can be supplied from the cathode solution tank 202, a pump was operated every one hour to supply water of about 3 cc to the cathode flow path 21. A liquid level sensor was provided to the cathode solution tank 202, and a discharge amount of water was measured.

Table 1 presents a current density, CO Faradaic efficiency, and $H_2$ Faradaic efficiency which were collected every about 3 hours. An amount as a result of removing the amount of water supplied to the cathode flow path 21 from the amount of discharge solution after 5.4 hours was detected as a value exceeding 1.1 with respect to the amount of water produced through the electrolysis, so that the refresh operation in which dried $CO_2$ gas was made to flow through both of the cathode 22 and the anode 11 for 3 minutes, was carried out. As the refresh operation, the $CO_2$ gas was made to flow through the cathode flow path 21 and the anode flow path 12 of the electrolysis cell 2, to thereby dry the cathode 22, the cathode flow path 21, the anode 11, and the anode flow path 12. After that, a KOH aqueous solution with 1 M was made to flow through the cathode flow path 21 and the anode flow path 12 to resume the $CO_2$ electrolysis operation. As presented in Table 1, after 6 hours, the entire current density became 227 mA/cm$^2$, and the CO Faradaic efficiency became 95%, and thus it was confirmed that the cell output is recovered by the refresh operation. After 9 hours, the entire current density was 220 mA/cm$^2$, and the CO Faradaic efficiency was 94%.

Example 2

In Example 2, there was provided a liquid sensor for measuring a refractive index of light inside the discharge flow path connected to the cathode 22. This sensor is a sensor that optically detects a passage of liquid through the discharge flow path based on a change in the refractive index, and it is possible to set an integrated time during which the refractive index was changed and the passage of liquid occurred, as a discharge amount. An experiment was conducted under conditions similar to those of Example 1 other than that.

Table 1 presents a current density, CO Faradaic efficiency, and $H_2$ Faradaic efficiency which were collected every about 3 hours. Similarly to Example 1, an amount as a result of removing the amount of water supplied to the cathode flow path 23 from the discharge amount after 5.4 hours was detected as a value exceeding 1 with respect to the amount of water produced through the electrolysis, so that the refresh operation was carried out. After 6 hours, the entire current density became 227 mA/cm$^2$, and the CO Faradaic efficiency became 95%, and thus it was confirmed that the cell output is recovered by the refresh operation. After 9 hours, the entire current density was 220 mA/cm$^2$, and the CO Faradaic efficiency was 94%.

Example 3

In a configuration similar to that of Example 1, a concentration sensor was provided to the cathode solution tank 202 to measure a potassium concentration of a discharge solution. An experiment was conducted under conditions similar to those of Example 1 other than that.

Table 1 presents a current density, CO Faradaic efficiency, and $H_2$ Faradaic efficiency which were collected every about 3 hours. After 5.5 hours, a concentration of potassium in the cathode solution tank 202 was lower than a value obtained by multiplying 0.9 with respect to a value as a result of dividing a potassium amount with the number of moles same as a charge transfer amount by an amount of liquid obtained by adding an amount of water produced through the electrolysis and an amount of water supplied to the cathode flow path 21, and thus the refresh operation was carried out. As the refresh operation, the $CO_2$ gas was made to flow through the cathode flow path 21 and the anode flow path 12, to thereby dry the cathode 22, the cathode flow path 21, the anode 11, and the anode flow path 12. After that, a KOH aqueous solution with 1 M was made to flow through the cathode flow path 21 and the anode flow path 12 to resume the $CO_2$ electrolysis operation. As presented in Table 1, the entire current density became 227 mA/cm$^2$ after 6 hours, and the CO Faradaic efficiency became 95% after 6 hours, and thus it was confirmed that the cell output is recovered by the refresh operation. After 9 hours, the CO Faradaic efficiency was 94%.

Example 4

Next, as in FIG. 14 which illustrates the structure of the carbon dioxide electrolysis cell, the cathode current collector 24, the cathode flow path 23, the cathode 22, the separator 30, the anode 11, the anode flow path 12, and the anode current collector 13 were stacked in this order from the top, the stack was sandwiched to be formed as a carbon dioxide electrolysis cell. For the separator, a PTFE porous body (product name: POREFLON) after being subjected to hydrophilic treatment was used. Note that an evaluation temperature was the room temperature. An experiment was conducted similarly to Example 1 other than that.

Table 1 presents a current density, CO Faradaic efficiency, and $H_2$ Faradaic efficiency which were collected every about 3 hours. An amount as a result of removing the amount of water supplied from a cathode inlet from the amount of discharge solution of the cathode after 5.2 hours was detected as a value exceeding 1.2 with respect to the amount of water produced through the electrolysis, so that the refresh operation was carried out. As the refresh operation, the $CO_2$ gas was made to flow through the cathode flow path 23 and the anode flow path 12, to thereby dry the cathode 22, the cathode flow path 23, the anode 11, and the anode flow path 12. After that, a KOH aqueous solution with 1 M was made to flow through the cathode flow path 23 and the anode flow path 12 to resume the $CO_2$ electrolysis operation. As presented in Table 1, after 6 hours, the entire current density became 248 mA/cm$^2$, and the CO Faradaic efficiency became 95%, and thus it was confirmed that the cell output is recovered by the refresh operation. After 9 hours, the entire current density was 228 mA/cm$^2$, and the CO Faradaic efficiency was 94%.

Example 5

An operation of returning the cathode discharge solution to the anode flow path 12 was conducted after the refresh operation. An experiment was conducted similarly to Example 4 other than that. Results are presented in Table 1.

Comparative Example 2

An experiment was conducted under conditions similar to those of Example 1 except that the refresh operation was continuously performed every 12 hours. Table 1 presents a current density, CO Faradaic efficiency, and $H_2$ Faradaic efficiency which were collected every about 3 hours.

As can be understood from Examples 1 to 5, and Comparative Examples 1 and 2, by performing the refresh operation based on the data acquired by the sensor, it is possible to improve the current density, the CO Faradaic efficiency, the $H_2$ Faradaic efficiency, and the like. This indicates that the cell performance can be maintained for a longer period of time when compared to the prior art.

TABLE 1

|  |  | Operating Time | | | | | |
| --- | --- | --- | --- | --- | --- | --- | --- |
|  |  | 0 h | 3 h | 6 h | 9 h | 12 h | 24 h |
| Example 1 | Current density (mA/cm$^2$) | 245 | 223 | 227 | 220 | — | — |
|  | Faradaic efficiency of CO (%) | 96 | 94 | 95 | 94 | — | — |
|  | Faradaic efficiency of $H_2$ (%) | 1 | 2.5 | 2.6 | 2.8 | — | — |
| Example 2 | Current density (mA/cm$^2$) | 245 | 223 | 227 | 220 | — | — |
|  | Faradaic efficiency of CO (%) | 96 | 94 | 95 | 94 | — | — |
|  | Faradaic efficiency of $H_2$ (%) | 1 | 2.5 | 2.6 | 2.8 | — | — |
| Example 3 | Current density (mA/cm$^2$) | 245 | 223 | 227 | 220 | — | — |
|  | Faradaic efficiency of CO (%) | 96 | 94 | 95 | 94 | — | — |
|  | Faradaic efficiency of $H_2$ (%) | 1 | 2.5 | 2.5 | 2.7 | — | — |
| Example 4 | Current density (mA/cm$^2$) | 260 | 230 | 248 | 228 | — | — |
|  | Faradaic efficiency of CO (%) | 97 | 94 | 95 | 94 | — | — |
|  | Faradaic efficiency of $H_2$ (%) | 1.1 | 2.7 | 2.1 | 2.8 | — | — |
| Example 5 | Current density (mA/cm$^2$) | 260 | 230 | 248 | 228 | 246 | 244 |
|  | Faradaic efficiency of CO (%) | 97 | 94 | 95 | 94 | 95 | 93 |
|  | Faradaic efficiency of $H_2$ (%) | 1.1 | 2.7 | 2.1 | 2.8 | 2.3 | 3.5 |
| Comparative Example 1 | Current density (mA/cm$^2$) | 245 | 223 | 210 | 207 | 203 | 201 |
|  | Faradaic efficiency of CO (%) | 96 | 94 | 91 | 89 | 88 | 86 |
|  | Faradaic efficiency of $H_2$ (%) | 1 | 2.5 | 4.5 | 6.7 | 7.8 | 8.8 |
| Comparative Example 2 | Current density (mA/cm$^2$) | 260 | 230 | 225 | 216 | 206 | 204 |
|  | Faradaic efficiency of CO (%) | 97 | 94 | 93 | 91 | 89 | 88 |
|  | Faradaic efficiency of $H_2$ (%) | 1.1 | 2.7 | 5.1 | 7 | 8.3 | 9 |

Table 1 presents a current density, CO Faradaic efficiency, and $H_2$ Faradaic efficiency which were collected every about 3 hours. The refresh operation was performed after 5.2 hours, after 10.1 hours, after 14.9 hours, and after 19.7 hours, respectively, and the cathode discharge solution was returned to the anode flow path 12.

After 12 hours, the entire current density became 246 mA/cm$^2$, and the CO Faradaic efficiency became 95%, and thus it was confirmed that the cell output is recovered by the refresh operation. After 24 hours, the entire current density was 244 mA/cm$^2$, and the CO Faradaic efficiency was 93%.

Comparative Example 1

An experiment was conducted under conditions similar to those of Example 1 except that the refresh operation was not performed. Table 1 presents a current density, CO Faradaic efficiency, and $H_2$ Faradaic efficiency which were collected every about 3 hours.

Note that configurations of the above-described respective embodiments may be each applied in combination, and further may be partially substituted. Herein, while certain embodiments of the present invention have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the invention.

What is claimed is:

1. A carbon dioxide electrolytic device, comprising:
   an electrolysis cell including
      a cathode to reduce a first substance containing carbon dioxide and thus produce a first product containing a carbon compound,
      an anode to oxidize a second substance containing water or hydroxide ions and thus produce a second product containing oxygen,
      a cathode flow path facing the cathode,
      an anode flow path facing the anode, and
      a separator separating the anode and the cathode;

a carbon dioxide source to supply the carbon dioxide to the cathode flow path;
a solution source to supply an electrolytic solution containing water to the anode flow path;
at least one sensor to acquire at least one data selected from the group consisting of a data indicating a discharge amount per unit time of a liquid containing water to be discharged from at least one flow path selected from the group consisting of the anode and cathode flow paths and a data indicating a concentration of at least one ion selected from the group consisting of ions in the liquid;
a power controller to apply a voltage between the anode and the cathode;
a refresh material source including a gas source to supply a gaseous substance to the at least one flow path; and
a controller programmed to stop the supply of the carbon dioxide and the electrolytic solution, and start the supply of the gaseous substance from the refresh material source to the at least one flow path, in accordance with the at least one data.

2. The device according to claim 1, further comprising a flow path to supply the liquid to be discharged from the cathode flow path to the anode flow path through the solution source.

3. The device according to claim 2, further comprising:
a first tank connected to the cathode flow path and configured to store the liquid; and
a second tank connected to the anode flow path and configured to store the electrolytic solution.

4. The device according to claim 1, wherein:
the solution source has a tank to store a solution containing the liquid; and
the at least one sensor has a liquid level sensor to acquire a data indicating a height of a liquid surface of the solution in the tank.

5. The device according to claim 1, wherein
the at least one sensor has a sensor to acquire a data indicating a refractive index of light or a pressure inside the at least one flow path.

6. The device according to claim 1, wherein
a refresh material source further includes a solution supply source to supply a rinse solution to the at least one flow path, and
the controller programmed to supply the rinse solution from the solution supply source and the gaseous substance from the gas source to the at least one flow path exposed from the electrolytic solution.

7. The device according to claim 1, further comprising a flow rate controller controlled by the controller and configured to adjust a flow rate of at least one selected from the group consisting of the rinse solution and the gaseous sub stance.

8. The device according to claim 1, wherein
the gaseous substance contains at least one selected from the group consisting of air, carbon dioxide, oxygen, nitrogen, and argon.

9. A carbon dioxide electrolytic device, comprising:
an electrolysis cell including
a cathode to reduce a first substance containing carbon dioxide and thus produce a first product containing a first carbon compound,
an anode to oxidize a second substance containing water or hydroxide ions and thus produce a second product containing oxygen,
a cathode flow path facing the cathode,
an anode flow path facing the anode, and
a separator separating the anode and the cathode;
a carbon dioxide source to supply the carbon dioxide to the cathode flow path;
a solution source to supply an electrolytic solution containing the water to the anode flow path;
a power controller to apply a voltage between the anode and the cathode;
a refresh material source including a gas source to supply a gaseous substance to at least one flow path selected from the group consisting of the anode and cathode flow paths;
a reactor to produce a third product containing a second carbon compound by using the first product supplied through the cathode flow path;
a discharge flow path connected to the reactor;
at least one sensor to acquire at least one data selected from the group consisting of a data indicating a discharge amount per unit time of a liquid containing water to be discharged from the discharge flow path and a data indicating a concentration of at least one ion selected from the group consisting of ions in the liquid; and
a controller programmed to stop the supply of the carbon dioxide and the electrolytic solution, and start the supply of the gaseous substance from the refresh material source to the at least one flow path, in accordance with the at least one data.

10. The device according to claim 9, further comprising a tank connected to the discharge flow path and configured to store the liquid, wherein
the at least one sensor has a liquid level sensor to acquire a data indicating a height of a liquid surface of the liquid in the tank.

11. The device according to claim 9, wherein
the at least one sensor has a sensor to acquire a data indicating a refractive index of light or a pressure inside the discharge flow path.

12. A method of electrolyzing carbon dioxide, comprising:
supplying carbon dioxide to a cathode flow path facing a cathode to reduce a first substance containing the carbon dioxide and thus produce a first product containing a carbon compound, and supplying an electrolytic solution containing water to an anode flow path facing an anode to oxidize a second substance containing water or hydroxide ions and thus produce a second product containing oxygen;
applying a voltage between the cathode and the anode to reduce the first substance and thus produce the first product on the cathode, and to oxidize the second substance and thus produce the second product on the anode;
acquiring at least one data selected from the group consisting of a data indicating a discharge amount per unit time of a liquid containing water to be discharged from at least one flow path selected from the group consisting of the anode and cathode flow paths and a data indicating a concentration of at least one ion selected from the group consisting of ions in the liquid; and
stopping the supply of the carbon dioxide and the electrolytic solution, and starting supply of a gaseous substance to the at least one flow path, in accordance with the at least one data.

13. A method of electrolyzing carbon dioxide, comprising:
- supplying carbon dioxide to a cathode flow path facing a cathode to reduce a first substance containing the carbon dioxide and thus produce a first product containing a first carbon compound, and supplying an electrolytic solution containing water to an anode flow path facing an anode to oxidize a second substance containing water or hydroxide ions and thus produce a second product containing oxygen;
- applying a voltage between the cathode and the anode to reduce the first substance and thus produce the first product on the cathode, and to oxidize the second substance and thus produce the second product on the anode;
- supplying the first product to a reactor through the cathode flow path, and producing a third product containing a second carbon compound by using the first product;
- acquiring at least one data selected from the group consisting of a data indicating a discharge amount per unit time of a liquid containing water to be discharged from the reactor and a data indicating a concentration of at least one ion selected from the group consisting of ions in the liquid; and
- stopping the supply of the carbon dioxide and the electrolytic solution, and starting supply of a gaseous substance to at least one flow path selected from the group consisting of the anode and cathode flow paths, in accordance with the at least one data.

14. The method according to claim 12, further comprising supplying a rinse solution to the at least one flow path.

* * * * *